United States Patent [19]

Weisman et al.

[11] Patent Number: 4,773,903
[45] Date of Patent: Sep. 27, 1988

[54] COMPOSITE ABSORBENT STRUCTURES

[75] Inventors: Paul T. Weisman, Fairfield; Thomas H. Daugherty, Cincinnati, both of Ohio; Thomas I. Insley, Jr., Lake Elmo, Minn.

[73] Assignees: The Procter & Gamble Co., Cincinnati, Ohio; Minnesota Mining and Manufacturing Company, St. Paul, Minn.

[21] Appl. No.: 57,599

[22] Filed: Jun. 2, 1987

[51] Int. Cl.⁴ .............................................. A61F 13/16
[52] U.S. Cl. ..................................... 604/368; 604/370
[58] Field of Search ............... 604/368, 369, 370, 366, 604/365, 372, 358; 428/171, 172, 221, 224, 283

[56] References Cited

U.S. PATENT DOCUMENTS

| | | | |
|---|---|---|---|
| 3,016,599 | 1/1962 | Perry | 28/78 |
| 3,971,373 | 7/1976 | Braun . | |
| 4,100,324 | 7/1978 | Anderson et al. | 428/288 |
| 4,103,058 | 7/1978 | Humlicek | 428/171 |
| 4,118,531 | 10/1978 | Hauser | 428/224 |
| 4,307,143 | 12/1981 | Meitner | 252/91 |
| 4,381,782 | 5/1983 | Mazurak et al. | 604/368 |
| 4,429,001 | 1/1984 | Kolpin et al. | 428/283 |
| 4,468,428 | 8/1984 | Early et al. | 428/221 |
| 4,604,313 | 8/1986 | McFarland et al. | 428/172 |
| 4,610,678 | 9/1986 | Weisman et al. | 604/368 |
| 4,650,479 | 3/1987 | Insley | 604/358 |
| 4,654,039 | 3/1987 | Brandt et al. | 604/368 |

FOREIGN PATENT DOCUMENTS 156649 10/1985 European Pat. Off. .
2113731A 8/1983 United Kingdom .

Primary Examiner—John D. Yasko
Attorney, Agent, or Firm—George W. Allen; Jerry J. Yetter; Richard C. Witte

[57] ABSTRACT

The present invention relates to composite absorbent structures suitable for incorporation into absorbent articles such as sanitary napkins, diapers, training pants and the like. Such structures comprise webs of entangled blown microfibers, substantially non-absorbent crimped staple fibers, particles of certain types of hydrogel-forming polymeric gelling agents and hydrophilizing agent. Such composite web structures of this construction have especially desirable comfort, integrity and absorbency characteristics.

20 Claims, 4 Drawing Sheets

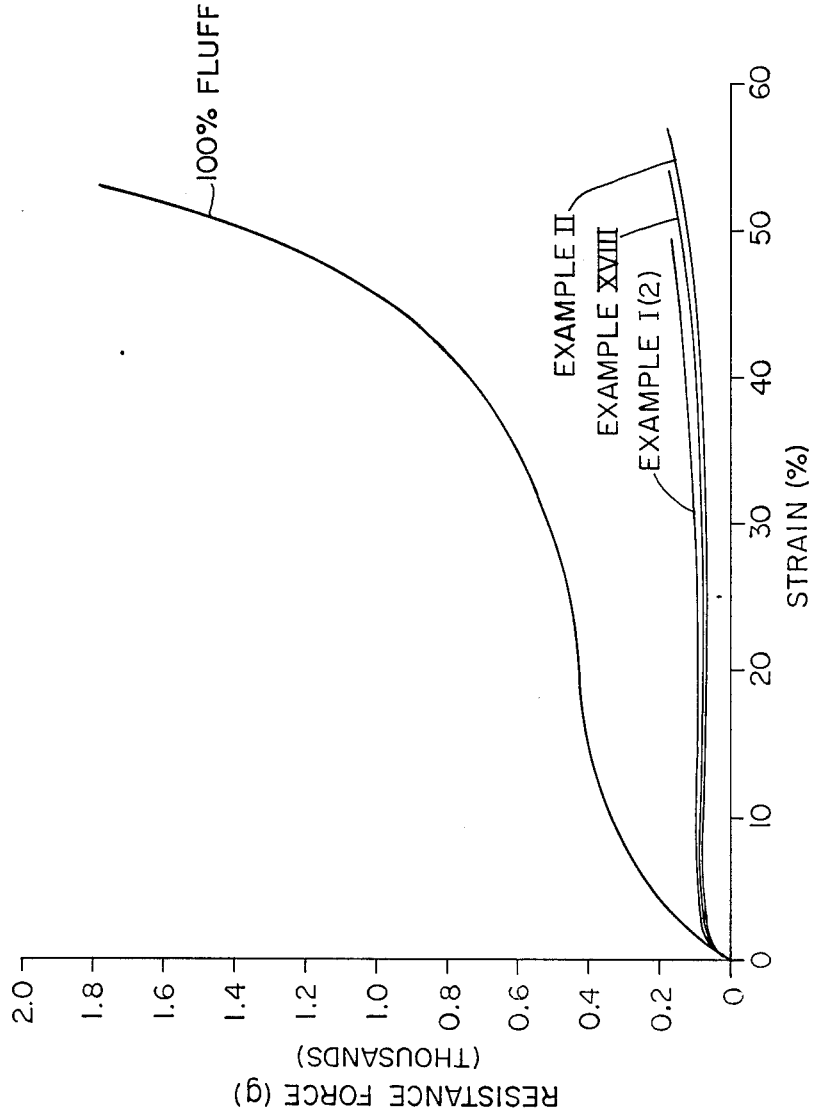

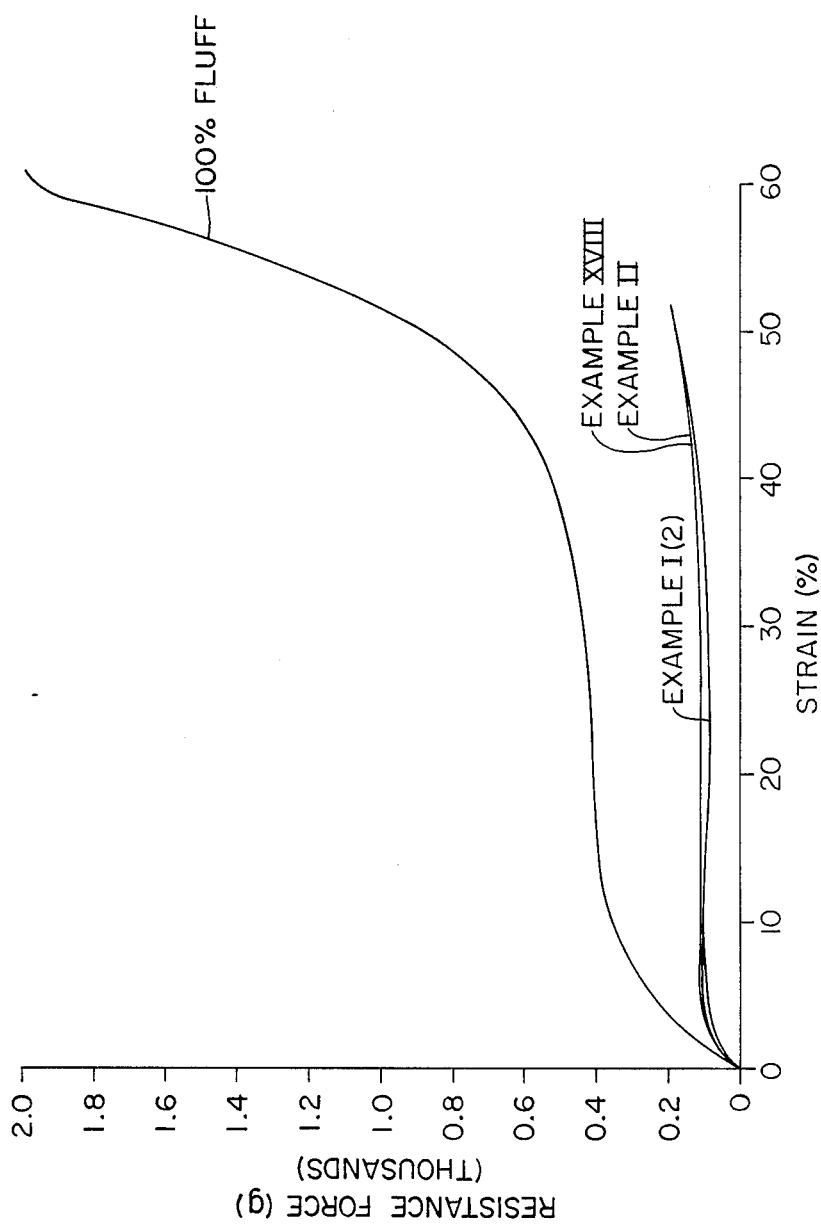

COMPOSITE ABSORBENT STRUCTURES

BACKGROUND OF THE INVENTION

The present invention relates to composite structures suitable for absorbing discharged body fluids. Such structures can be incorporated into disposable absorbent articles such as sanitary napkins, infant diapers, adult incontinence pads and the like.

Absorbent structures which comprise entangled masses of fibers, i.e., fibrous webs, are well known in the art. Such structures can imbibe liquids, such as discharged body fluids, both by an absorption mechanism wherein fluid is taken up by the fiber material itself and by a wicking mechanism wherein fluid is acquired by, distributed through and stored in the capillary interstices between fibers. One means for increasing the absorbent capacity of such fibrous web structures is to incorporate therein so-called superabsorbent polymers which imbibe fluid to thereby form a swollen hydrogel material. The resulting hydrogel serves to retain fluid within the structure. An absorbent structure of this type wherein hydrogel-forming materials in particulate (including fiber) form are incorporated into fibrous webs is disclosed in Weisman and Goldman; U.S. Pat. No. 4,610,678; Issued Sept. 9, 1986.

While absorbent capacity is a significant factor in determining the suitability of absorbent structures for use in disposable absorbent articles, other factors can also be important. For disposable absorbent articles which are worn or positioned in a particular relationship to the user's body, physical properties of the absorbent structures utilized in such articles are likewise relevant considerations. Thus features such as flexibility; resilience, e.g., resistance to bunching; softness; and tear resistance must generally be taken into account when selecting appropriate types of absorbent structures for use in absorbent articles. Absorbent structure properties which determine the comfort of the absorbent articles incorporating such structures are especially important in products like sanitary napkins wherein the intimate contact of the article with the wearer's body make the comfort properties of such structures especially noticeable.

One way of imparting strength and flexibility to fibrous web absorbent structures has involved the use of blown microfibers in combination with staple absorbent fibers to fashion absorbent products. Anderson et al, U.S. Pat. No. 4,100,324; Issued July 11, 1978, for example, discloses preparation of absorbent "fabrics" fashioned from blown microfibers and wood pulp fibers. Technology has also been developed to enhance the absorbent capacity of microfiber/stable fiber webs by incorporating therein particles of fluid-absorbent polymeric material. For example, Kimberly-Clark Ltd., British Patent Spec. No. 2,113,731A, Published Aug. 10, 1983; Kolpin/Brownlee, U.S. Pat. No. 4,429,001, Issued Jan. 31, 1984 and Minnesota Mining & Manufacturing Company, European Patent Application EP-A-156649, Published Oct. 2, 1985 all disclose sorbent sheet materials which comprise webs of entangled blown microfibers, generally absorbent staple fibers and particles of solid, high-sorbency, liquid-sorbent polymer materials.

Notwithstanding the existence of such microfiber-based prior art absorbent structures, there is a continuing need to identify additional absorbent structures which contain microfibers and staple fibers in order to provide strength, integrity and resilience and which also contain liquid-sorbing polymeric material in order to provide absorbent capacity. There is also a need to identify structures of this type which especially desirable comfort properties. Accordingly, it is an object of the present invention to provide improved absorbent structures comprising certain types of blown microfibers, staple fibers and liquidsorbing polymeric material.

It is a further object of the present invention to provide absorbent structures which have acceptably high absorbent capacity but which are also exceptionally resistant to tearing and bunching, and which are especially flexible and resilient.

It is a further object of the present invention to provide disposable absorbent articles such as sanitary napkins, diapers, training pants, incontinence pads and the like which utilize such improved absorbent structures to form their absorbent cores.

SUMMARY OF THE INVENTION

The present invention is directed to a certain type of absorbent composite structure suitable for use in disposable absorbent articles of improved comfort, integrity and absorbency characteristics. Such composite structures comprise (a) from about 10% to 85% by weight of blown microfibers, (b) from about 10% to 85% by weight of substantially non-absorbent synthetic staple fibers, (c) from about 5% to 60% by weight of particles of a polymeric gelling agent, and (d) from about 0.1% to 10% by weight of a hydrophilizing agent.

The blown microfibers essentially present in such structures can range in diameter between about 1 and 50 microns. The nonabsorbent staple fibers can have a denier varying between about 5 and 70 and a percent crimp of at least about 15%. Both microfibers and staple fibers are formed from synthetic polymeric material having a modulus value, when dry, of at least about $0.1 \times 10^{10}$ dynes/cm$^2$. The modulus value of both the microfiber polymer and the staple fiber polymer should not significantly diminish when these fibers are wetted. Microfibers and staple fibers, hdyrophilized with the hydrophilizing agent, are preferably present in such structures in amounts such that the weight ratio of the microfiber component to the staple fiber component ranges from about 1:3 to 3:1.

The polymeric gelling agent material in such structures has a gel volume of at least about 20 grams of artificial menses per gram of gelling agent at equilibrium (one hour), a gel volume at two minutes which is at least 40% of the equilibrium gel volume and an extractable polymer content in synthetic urine of no more than about 17% by weight. The particles of the polymeric gelling agent generally range in diameter between about 30 microns and 2 mm.

In the composite structures of the present invention, the microfiber, staple fiber and polymeric gelling agent particles are combined, generally in a substantially unbonded manner, such that the resulting composite web has a dry density of from about 0.006 to 0.10 gram per cm$^3$. Preferably such a web will be formed into a structure having longitudinal, transverse and thickness dimensions. Such webs will generally exhibit both wet and dry resilience properties which enable such a composite web to recover to a dimension which is at least 50% of its original transverse dimension after being compressed to a transverse dimension which is 40% of its original transverse dimension.

BRIEF DESCRIPTION OF THE DRAWINGS

FIGS. 6 and 7 are graphic representations of the flexibility characteristics of the composite absorbent structures of the present invention, illustrated in terms of resistance measured as a function of strain during edgewise compression.

DETAILED DESCRIPTION OF THE INVENTION

Figure 1:
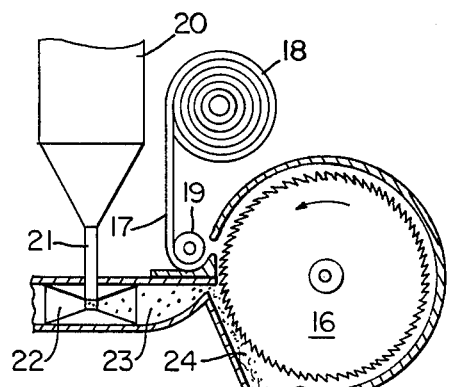
FIG. 1 is a schematic diagram of apparatus used in preparing the composite absorbent structures of this invention.
Figure 1:
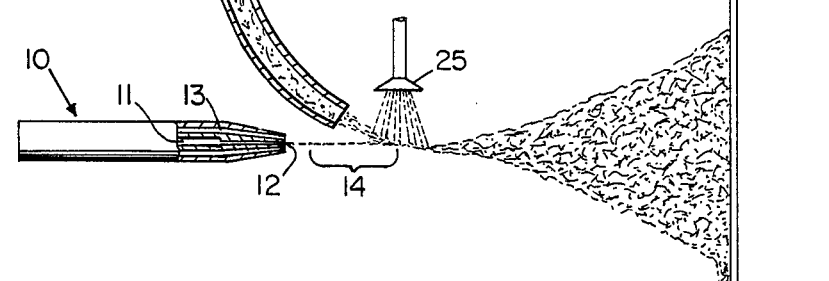
Figure 1:

The absorbent structures of the present invention are composites which contain both fibrous and non-fibrous components. For purposes of this invention, the terms "fibers" and "fibrous" refer to a specific type of "particulate" material wherein the length to diameter ratio of such particulate material is greater than about 50. "Non-fibrous" particles, conversely, are those wherein the length to diameter ratio is less than about 50.

One essential fibrous component of the composite absorbent structure herein comprises blown microfibers formed from synthetic polymeric material that provides fibers of particular size and stiffness characteristics. Blown microfibers are very fine fibers prepared by extruding liquified, fiber-forming polymer through orifices in a die into a high velocity gaseous stream. Fibers are attenuated by the gaseous stream and are subsequently solidified. The resulting stream of solidified fibers can be collected, e.g., on a screen disposed in the gaseous stream, as an entangled coherent fibrous mass. Such an entangled fibrous mass is characterized by extreme entanglement of the microfibers. This entanglement provides coherency and strength to the resulting web structure and also adapts the composite web structure to contain and retain particulate polymeric gelling agent and staple fibers. The microfibers are entangled sufficiently that is it generally impossible to remove one complete microfiber from the mass of microfibers or to trace one microfibers from beginning to end. The theoretical aspect ratio (ratio of length to diameter) of blown microfibers in the web structures herein approaches infinity, although significant discontinuity of the microfibers can occur during composite preparation.

Blown microfibers useful herein may be either melt-blown or solution-blown. Melt-blown fibers are those which are liquified by heating the desired fiber-forming polymeric material in order to form the extruded microfibers. Melt-blown fibers are preferred for use in forming the composite structures of the present invention. However, solution-blown fibers in which the fiberforming material is liquified by inclusion of a volatile solvent, can also be used. Carey, Jr., U.S. Pat. No. 4,011,067, Issued Mar. 8, 1977 incorporated herein by reference, discloses apparatus and procedures for preparing webs of blown microfibers. Microfibers will frequently be generally cylindrical in shape but other fiber geometries are also possible, e.g., wherein crosssections of microfibers are elliptical, rectangular, triangular, etc.

The blown microfibers which form an essential component of the composite absorbent structures herein must have certain size and stiffness characteristics in order to impart the requisite flexibility, integrity and resilience features to such absorbent structures. In particular, substantially all of the individual blown microfibers included in the structures herein should have a diameter less than about 50 microns. More preferably the microfibers will have an average diameter ranging from about 1 to 10 microns. For purposes of the present invention, microfiber diameter can be determined from microfiber cross-sectional area, calculated by assuming that such cross-sectional area is circular.

The microfibers utilized should also meet certain stiffness requirements. Microfiber stiffness is a function of both fiber geometry and the type of polymeric material used to form the microfiber. For purposes of the present invention, microfiber stiffness can be quantified by specifying a modulus value for the microfiber polymer material along with fiber geometry and size as hereinbefore described. The modulus of the microfiber polymer material, e.g., the modulus of elasticity or tensile modulus, is in general defined as the ratio of change in stress to change in strain when a given amount of stress is applied to a sample of polymeric material. Thus this modulus is usually characterized as a slope of the initial portion of the stress versus strain curve when strain is plotted as a function of applied stress for a given piece of polymeric material.

Determination of the modulus of the microfiber polymer material can be carried out in a variety of ways on materials in fiber form as outlined in the *Handbook of Physical and Mechanical Testing for Paper and Paperboard*, Vol. 1; Richard E. Mark, Editor; Marcel Dekker, Inc.; 1983, pp 447–456 and p 465, incorporated herein by reference. Measurements of imposed strain and the resulting stress response can be carried out using, for example, Instron or Dynamic Mechanical Analyzer apparatus. Modulus determinations do not need to be carried to on materials which are actually in fiber form. Indeed, direct measurement of modulus by testing of individual microfibers is not necessary. Instead, modulus values can and frequently are determined by testing polymeric materials in any convenient configuration, e.g., larger fibers, strips, pellets, etc.

For purposes of the present invention, modulus values for the microfiber material are determined at room temperature, i.e., at 20° C. Microfibers useful herein are those which are prepared from polymers that have modulus values of at least about $0.1 \times 10^{10}$ dynes/cm$^2$, more preferably from about $0.5 \times 10^{10}$ to $3.5 \times 10^{10}$ dynes/cm$^2$. Generally the polymeric material used to form such microfibers is, in and of itself, relatively non-absorbent. Thus the modulus value for the microfiber material will generally fall within the foregoing ranges whether the microfibers are wet or dry. It is, in fact, essential that the modulus of the microfiber material not diminish significantly when the microfibers are wetted. For purposes of this invention, this means that the modulus of the microfiber material when wet should be at least about 70% of the modulus of the dry material, more preferably at least 80% of the dry modulus value. Such microfiber material is considered as wetted after it has been soaked, i.e., saturated with menstrual fluid or synthetic urine.

In order to realize microfibers of the required size and stiffness, the microfibers useful in the structures herein can be prepared from a synthetic polymer material which has a melting point of from about 100° C. to 265° C. and which will provide microfibers of the requisite diameter. Synthetic polymer materials having such characteristics include, for example, polyolefins, polyesters, polyamides, polyacrylics and polystyrenes. Specific examples of suitable polymeric material include polypropylene, polyethylene, polyethylene terephthalate (PET) and nylon. Polypropylene is highly preferred.

The blown microfiber component of the composite structures herein will generally comprise from about 10% to 85% by weight of the dry composite structure. More preferably, the microfiber component should comprise from about 20% to 65% by weight of the dry composite. For composite structures especially suitable for use in sanitary napkins, the microfiber component preferably comprises from about 30% to 50% by weight of the dry composite structure. For composite structures especially suitable for use in infant diapers, the microfiber component preferably comprises from about 30% to 70% by weight of the dry composite structure. For composite structures especially suitable for use in disposable training pants, the microfiber component preferably comprises from about 30% to 70% by weight of the dry composite structure. As discussed more fully hereinafter, the amount of microfiber component employed relative to the amount of staple fiber can also be important to the realization of composite structures of especially desirable comfort and absorbency properties.

A second essential fibrous component of the composite absorbent structures herein comprises substantially non-absorbent, crimped, synthetic staple fibers. The staple fibers, when combined with the microfibers hereinafter described, serve to impart desirable bulk, fluid acquisition characteristics and resilience properties to the composite absorbent structures of this invention. Substantially all of the staple fibers incorporated into the absorbent structures herein will preferably range in length from about 0.1 to 15 cm., more preferably from about 2 to 7 cm.

The individual staple fibers used in the compositions herein are in and of themselves substantially non-absorbent. Thus, such fibers must be prepared from synthetic polymer material which does not substantially swell or gel in the presence of fluids (e.g., urine, menses) encountered in disposable absorbent products. Accordingly, the synthetic staple fibers of the present invention, unlike the staple fibers used in several types of prior art absorbent webs, must have a water retention value (WRV) of less than about 15%, more preferably less than about 10% and even more preferably less than 5%. The water retention value is a measure of the amount of water absorbed by the staple fibers themselves; determination of WRVs for purposes of this invention is described in greater detail hereinafter. The absorbent structures of the present invention are preferably substantially free of absorbent staple fibers, e.g., cotton, rayon, cellulose, etc., which have WRV values of 15% or greater.

Suitable polymeric materials which do provide substantially non-absorbent fibers of the requisite WRV include polyesters, polyolefins, polyacrylics, polyamides, polystyrenes and the like. In particular, staple fibers made of polyethylene, polypropylene and polyethylene terephthalate (PET, i.e., "Dacron") are especially preferred.

The staple fibers used in the absorbent structures of this invention must be crimped in order for the resulting absorbent structures to have the requisite resilience and resistance to bunching during use in absorbent products. Crimped fibers are those which have a continuous wavy, curvy or jagged character along their length. Fiber crimping of this type is described more fully in Hauser; U.S. Pat. No. 4,118,531; Issued Oct. 3, 1978, incorporated herein by reference. As noted in this U.S. Pat. No. 4,118,531 crimped fibers of this type, which contribute to the desirable properties of absorbent structures containing them, are those which have a crimp count of at least two crimps per centimeter and a percent crimp of at least about 15%, preferably at least about 25%. Percent crimp is defined as the difference between the uncrimped length of the fiber (measured after fully straightening a sample fiber) and the crimped length (measured by suspending the sample fiber with a weight attached to one end equal to 2 mg. per decitex of the fiber, which straightens the large-radius bends of the fiber) divided by the crimped length and multiplied by 100.

The crimped synthetic staple fibers of the absorbent structures herein will generally have a denier ranging from about 5 to 70. More preferably the denier of the staple fibers will range between about 10 and 25.

In addition to particular size and crimping characteristics, the staple fibers of the structures of the present invention must also have certain stiffness characteristics. As with the microfibers used, staple fiber stiffness is a function of both fiber geometry and type of polymer material used to form the fiber. For purposes of the present invention, staple fiber stiffness, like stiffness of the microfibers used, can be quantified by specifying a fiber material modulus value along with fiber geometry and fiber size as hereinbefore described. The modulus value for material used to form staple fibers is defined in the same manner as the modulus value for the microfiber material as hereinbefore discussed. The staple fiber material used in the present invention will generally have a modulus value of at least about $0.1 \times 10^{10}$ dynes/cm$^2$, more preferably from about $2.5 \times 10^{10}$ to $3.5 \times 10^{10}$ dynes/cm$^2$. As with the microfibers employed, the substantially non-absorbent nature of the staple fibers means that there should be little significant difference in modulus of the staple fiber material whether the staple fiber material is wet or dry when the modulus is determined. Accordingly, the modulus value, both wet and dry, must fall within the ranges hereinbefore set forth for the staple fiber material. Furthermore, as with the microfiber material modulus, the modulus value of the dry staple fiber material must not significantly diminish when the staple fiber material is wetted.

Both the actual amount of staple fiber incorporated into the absorbent web structures of the present invention, as well as the amount of staple fibers relative to the microfiber component in such structures, can affect the absorbency, integrity, resilience and comfort properties of the resulting composite absorbent webs. Generally, the staple fiber component can comprise from about 10% to 85% by weight of the dry absorbent composite structures herein, more preferably from about 20% to 60% by weight of the dry composite structures. For composite structures especially suitable for use in sanitary napkins, the staple fiber component should comprise from about 25% to 55% by weight of the dry composite. For composite structures especially suitable for use in infant diapers, the staple fiber component preferably comprises from about 10% to 55% by weight of the dry composite. For composite structures especially suitable for use in disposable training pants, the staple fiber component will preferably comprise from about 10% to 55% by weight of the dry composite. The weight ratio of microfiber to staple fiber in such structures will preferably range from about 1:3 to 3:1, more preferably from about 3:7 to 7:3.

A third essential component of the composite absorbent structures herein comprises discrete non-fibrous particles of a hydrogel-forming, polymeric gelling agent. Hydrogel-forming polymeric materials of this type are those which, upon contact with fluids (i.e., liquids) such as water or body fluids, imbibe such fluids and thereby form hydrogels. In this manner, fluid discharged into the absorbent structures herein can be acquired and held by the particles of the polymeric gelling agent, thereby providing the structures herein with the requisite absorbent capacity.

The polymeric gelling agent particles used herein will generally comprise a substantially water-insoluble, slightly crosslinked, partially neutralized, hydrogel-forming polymer material. Such polymer materials can be prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids and mixtures thereof.

Olefinically unsaturated carboxylic acid and carboxylic acid anhydride monomers include the acrylic acids typified by acrylic acid itself, methacrylic acid, ethacrylic acid, alpha-chloroacrylic acid, alpha-cyano acrylic acid, bet a-methyl-acrylic acid (crotonic acid), alpha-phenyl acrylic acid, beta-acryloxy propionic acid, sorbic acid, alpha-chloro sorbic acid, angelic acid, cinnamic acid, p-chloro cinnamic acid, beta-styryl acrylic acid (1-carboxy-4-phenyl butadiene-1,3), itaconic acid, citraconic acid, mesaconic acid, glutaconic acid, aconitic acid, maleic acid, fumaric acid, tricarboxy ethylene and maleic acid anhydride.

Olefinically unsaturated sulfonic acid monomers include aliphatic or aromatic vinyl sulfonic acids such as vinylsulfonic acid, allyl sulfonic acid, vinyltoluenesulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-acryloxy propyl sulfonic acid, 2-hydroxy-3-methacryloxy propyl sulfonic acid and 2-acrylamido-2-metyl propane sulfonic acid.

Of all the foregoing unsaturated, acid-containing monomers, preferred monomers include acrylic acid, methacrylic acid, and 2-acrylamido-2-methyl propane sulfonic acid. Acrylic acid itself is especially preferred for preparation of the polymeric gelling agent material.

In the hydrogel-forming polymeric gelling agents used herein, the polymeric component formed from unsaturated, acid-containing monomers may be grafted on to other types of polymer moieties such as starch or cellulose. Acrylic acid grafted starch materials of this type are especially preferred for use herein.

Preferred polymer gelling agents which can be prepared from the foregoing types of monomers include hydrolyzed acrylonitrile grafted starch, acrylic acid grafted starch, polyacrylates, isobutylene maleic anhydride copolymers and combinations thereof. Especially preferred are the polyacrylates and acrylic acid grafted starch.

Whatever the nature of the basic polymer components of the hydrogel-forming polymeric gelling agents used herein, such materials will in general be slightly cross-linked. Cross-linking serves to render the hydrogel-forming polymer gelling agents used in this invention substantially water-insoluble, and cross-linking thus in part determines the gel volume and extractable polymer characteristics of the hydrogels formed from the polymeric gelling agents employed. Suitable cross-linking agents are well known in the art and include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer material; and (4) polyvalent metal compounds which can form ionic cross-linkages. Cross-linking agents of the foregoing types are described in greater detail in Masuda et al; U.S. Pat. No. 4,076,663; Issued Feb. 28, 1978, incorporated herein by reference. Preferred cross-linking agents are the dior polyesters of unsaturated mono-or polycarboxylic acids with polyols, the bisacrylamides and the di-or triallyl amines. Especially preferred cross-linking agents are N,N'-methylenebisacrylamide, trimethylol propane triacrylate and triallyl amine.

The cross-linking agent will generally comprise from about 0.001 mole percent to 5 mole percent of the resulting hydrogelforming polymer material. More preferably, the cross-linking agent will comprise from about 0.01 mole percent to 3 mole percent of the hydrogel-forming polymeric gelling agent used herein.

The slightly cross-linked, hydrogel-forming polymer gelling agents used in the present invention will generally be employed in their partially neutralized form. For purposes of this invention, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammoniun, substituted ammonium and amines. This percentage of the total monomers utilized which are neutralized acid group-containing monomers is referred to herein as the "degree of neutralization."

The polymeric gelling agent materials used in the structures herein must have a relatively high capacity for imbibing fluids encountered in absorbent structures and must also imbibe such fluid at a relatively fast rate. Both of these characteristics, capacity and uptake rate, can be quantified by referencing the "gel volume" of the polymeric gelling agents which are to be selected for use in the present invention.

For purposes of this invention, gel volume can be defined in terms of the amount of artificial menses absorbed by any given polymeric gelling agent and is specified as grams of artificial menses per gram of polymeric gelling agent in a procedure hereinafter defined. The artificial menses used to define gel volume herein is a mixture of sheep's blood and a synthetic mucous component. The preparation of artificial menses which can be used in making gel volume determinations is set forth hereinafter in the Test Methods section.

Gel volume can be determined by swelling samples of particles of polymeric gelling agent to be tested with artificial menses fluid. Samples of polymeric gelling agent are maintained in contact with the swelling fluid at ambient temperature for about one hour so that swelling equilibrium is attained. The swollen gel samples are then centrifuged to remove fluid not actually imbibed by the polymeric gelling agent. Using a procedure described in greater detail hereinafter in the Test Methods section, the gel volume of the polymeric gelling agent in grams of artificial menses per gram of polymeric gelling agent can then be calculated from experimentally determined measurements.

The polymeric gelling agent materials useful in the structures of the present invention are those which have an equilibrium (1 hour) gel volume of at least about 20 grams of artificial menses per gram of polymeric gelling agent. More preferably, the polymeric gelling agent materials which are useful have an equilibrium (1 hour) gel volume of from about 25 to 50 grams of artificial menses per gram of polymeric gelling agent. Polymeric gelling agent material having such relatively high gel volume characteristics are especially useful in absorbent structures herein since the hydrogels formed from such materials can, by definition, hold desirably high amounts of discharged body fluids such as menses and urine.

When the absorbent composite structures herein are to be used in infant diapers or training pants, the gel volume of the polymeric gelling agents employed in such structures can, and frequently will, be expressed in terms of grams of synthetic urine per gram of polymeric gelling agent instead of grams of artificial menses per gram of polymeric gelling agent. Gel volume in synthetic urine can be determined by forming a suspension of about 0.1-0.2 parts of dried polymeric gelling agent to be tested with about 20 parts of this synthetic urine. This suspension is maintained at ambient temperature under gentle stirring for about 1 hour so that swelling equilibrium is attained. Using a procedure described in greater detail hereinafter in the Test Methods section, the gel volume of the polymeric gelling agent in grams of synthetic urine per gram of polymeric gelling agent is then calculated from the weight fraction of the polymeric gelling agent in the suspension and the ratio of the liquid volume excluded from the formed hydrogel to the total of the suspension. The structures of the present invention which are to be used in diapers or training pants will generally employ polymeric gelling agents having a gel volume of from about 20 to 70 grams, more preferably from about 30 to 60 grams, of synthetic urine per gram of polymeric gelling agent.

In addition to their relatively high equilibrium (1 hour) gel volume, the hydrogels formed from the polymeric gelling agents used in the present invention must also be able to acquire and tie up fluid quickly. For this reason, the polymeric gelling agent materials useful herein must also have certain gel volume values after two minutes of fluid contact in addition to having the particular equilibrium, i.e., one hour, gel volume values specified hereinbefore. In particular, the polymeric gelling agents useful herein will generally have a two minute gel volume which is at least 40% of the equilibrium (1 hour) gel volume. More preferably the two-minute gel volume for the polymeric gelling agents herein will be at least 50% of the equilibrium (1 hour) gel volume.

Another feature of the polymeric gelling agents which are useful in the absorbent structures herein relates to the level of extractable polymer material present in such hydrogel-forming material. Extractable polymer levels can be determined by contacting a sample of hydrogel-forming polymeric gelling agent material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. Synthetic urine is utilized in such a procedure since extractable polymer content in synthetic urine is more readily determined than extractable polymer content in artificial menses. The particular procedure used to determine extractable polymer content of the polymeric gelling agents herein is set forth in Brandt, Goldman and Inglin; U.S. Pat. No. 4,654,039; Issued Mar. 31, 1987, incorporated herein by reference. Polymeric gelling agent materials especially useful in the absorbent structures herein are those which have an equilibrium extractables content in synthetic urine of no more than about 17%, preferably no more than about 10% by weight of the polymeric gelling agent.

The polymeric gelling agent materials hereinbefore described can be incorporated into the absorbent structures of the present invention in the form of discrete particles. Such polymeric gelling agent particles can be of any desired shape, e.g., spherical or semi-spherical, cubic rod-like polyhedral, etc. Shapes having a large greatest dimension/smallest dimension ratio, like needles and flakes are also contemplated for use herein. Agglomerates of polymeric gelling agent particles may also be used.

Although the absorbent structures herein are expected to perform well with polymeric gelling agent particles having a particle size varying over a wide range, other considerations may preclude the use of very small or very large particles. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Preferred for use herein are polymeric gelling agent particles substantially all of which have a particle size of from about 30 microns to about 2 mm. "Particle Size" as used herein means the weighted average of the smallest dimension of the individual particles.

The amount of polymeric gelling agent particles used in the absorbent structures herein can be most conveniently expressed in terms of a weight percentage of the absorbent structure. Thus, the absorbent structures herein will generally contain from about 5% to 60%, more preferably from about 15% to 50%, by weight of the polymeric gelling agent particles. For composite structures especially suitable for use in sanitary napkins, the polymeric gelling agent component should comprise from about 15% to 30% by weight of the dry composite. For composite structures especially suitable for use in infant diapers, the polymeric gelling agent should comprise from about 15% to 50% by weight of the dry composite. For composite structures especially suitable for use in disposable training pants, the polymeric gelling agent preferably comprises from about 15% to 50% by weight of the dry composite.

The polymeric gelling agent particles may be distributed in a substantially uniform manner throughout the absorbent structures of the present invention. Alternatively, the polymeric gelling agent (PGA) may be non-uniformly distributed, for example, incorporated into discrete areas of relatively higher or lower PGA concentration. Thus, for instance, structures can be prepared with a PGA concentration gradient from the topsheet side to the backsheet side of the structure.

Another essential component of the absorbent structures herein is a hydrophilizing agent which is applied to the synthetic microfiber and staple fiber components to enhance the wettability of these fibers. Materials of this type are well-known in the art and can comprise, for example, surfactant materials or colloidal silica. If a surfactant is employed as the hydrophilizing agent, the type of surfactant can be anionic, cationic or nonionic with nonionic materials being especially preferred. Suitable nonionic surfactant include the ethoxylated alcohols and ethoxylated alkylphenols.

The hydrophilizing agent, in either solid or liquid form, can be applied to the synthetic microfibers and staple fibers of the absorbent structures herein at any convenient stage before, during or after preparation of such structures. Thus the hydrophilizing agent may be applied to the microfibers and staple fibers before they are comingled to form the absorbent web structures herein. Alternatively, the hydrophilizing agent amy be added to the comingled mass of microfibers and staple fibers used in forming the absorbent web structures herein. Hydrophilizing agent may furthermore be compounded with the microfiber-forming material before the microfibers are formed.

Hydrophilizing agent may also be applied to the web structures after such structures have been formed, for example, by spraying liquid, non-aqueous, nonionic surfactant onto the formed web structures. No matter how or when hydrophilizing agent is incorporated into the structures herein, hydrophilizing agent will generally comprise from about 0.01% to 10% by weight of the finished absorbent web structures, more preferably from about 0.01% to 5% by weight of such structures.

The absorbent web structures of the present invention can be prepared by forming a gaseous e.g., air, stream which comprises the blown microfiber, staple fiber, particulate polymeric gelling agent and hydrophilizing agent components, and by conveying this fiber and particle-containing stream to a collector device wherein an entangled mass of fibers and particles is air-laid as a continuous fibrous web. Apparatus for carrying out such a process can include conventional fiber blowing structures as taught, for example, in Wente, "Superfine Thermoplastic Fibers", *Industrial Engineering Chemistry*, Vol. 48, pages 1342 et seq (1956), or in Report No. 4364 of the Naval Research Laboratories, published May 25, 1954, entitled "Manufacture of Superfine Organic Fibers" by Wente et al. These publications are incorporated herein by reference.

Typical apparatus for preparing melt blown microfiber-based web structures of the present invention is schematically illustrated in FIG. 1 of the drawings submitted herewith. The apparatus of FIG. 1 includes a die, 10, which has an extrusion chamber, 11, through which liquified microfiber-forming material is advanced; die orifices, 12, arranged in line across the forward end of the die and through which the microfiber-forming material is extruded; and cooperating gas orifices, 13, through which a gas, typically heated air, is forced at very high velocity. The high-velocity gaseous stream draws out and attenuates the extruded microfiber-forming material, whereupon the microfiber-forming material solidifies as microfibers during travel through region, 14, to a collector, 15. The collector, 15, is typically a finely perforated screen, which in this case is in the form of a closedloop belt, but which can take alternative forms, such as a flat screen or a drum or cylinder. Gas-withdrawal apparatus may be positioned behind the screen to assist in deposition of fibers and removal of gas. Alternatively, two dies may be used and arranged so that the streams of melt blown microfibers issuing from them intersect to form one stream that continues to a collector, 15.

The apparatus shown in FIG. 1 also includes means for introducing polymeric gelling agent particles and non-absorbent staple fibers into the absorbent composite structures of the present invention. The staple fibers are introduced into the stream of melt blown microfibers through the use of a lickerin roll, 16. A web, 17, of crimped staple fibers, typically a loose, nonwoven web such as prepared on a garnet machine or "RandoWebber", is supplied from a supply roll, 18, under a drive roll, 19, where the leading edge engages against the lickerin roll, 16. The lickerin roll, 16, turns in the direction of the arrow and picks the crimped staple fibers from the leading edge of the web, 17, dissociating the crimped staple fibers from one another. The polymeric gelling agent particles are supplied from a particulate hopper, 20, through an inductor, 21, which meters the amount of particles flowing into a venturi, 22, which is in duct, 23. An air stream flows through duct, 23, for conveying the polymeric gelling agent particles. The polymer gelling agent particles are conveyed to inclined duct, 24, where the fluidized stream of polymeric gelling agent particles becomes the carrier stream for the crimped staple fibers delivered by the lickerin roll, 16. The polymeric gelling agent particles and crimped staple fibers are conveyed in the air stream through inclined duct, 24, and into the stream of melt blown microfibers where the polymeric gelling agent particles and crimped staple fibers become mixed with the melt blown microfibers. The mixed stream of melt blown microfibers, crimped staple fibers and polymeric gelling agent particles then continues to the collector, 15, where a web of randomly intermixed and intertangled microfibers, crimped staple fibers and polymeric gelling agent particles is formed. A spray jet, 25, may be used to apply the required hydrophilizing agent, e.g., a surfactant, to the mixed stream of blown microfibers, polymeric gelling agent particles and crimped staple fibers prior to collection at collector, 15.

The absorbent composite web structures prepared using such apparatus generally comprise intermingled or entangled masses of hydrophilized microfibers, crimped staple fibers and polymeric gelling agent particles. Such intermingled or entangled masses are substantially unbonded in the sense that they are substantially free of significant amounts of fibers and particles bonded to each other by chemical or fusion bonds. Thus, staple fibers and polymeric gelling agent particles should be combined with the microfiber stream after the microfibers have solidified to the point that substantially no interfiber or particle-fiber fusion bonds will be formed. Rather, the structural integrity of the composite web structures herein is generally maintained by the presence of mechanical or entanglement bonds throughout the structure.

Figure 2:
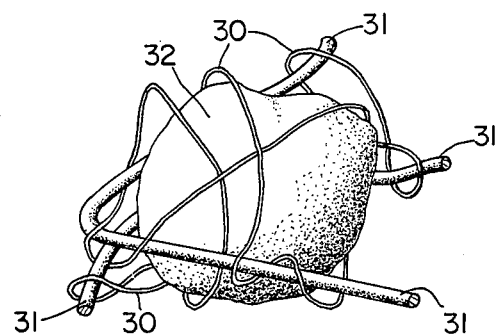
FIG. 2 is a greatly enlarged sectional representation of a portion of a composite absorbent structure of this invention.

FIG. 2 of the drawing submitted herewith illustrates the general structural relation ship of the microfiber, crimped staple fiber and polymeric gelling agent particle components in preferred composite webs of this invention. FIG. 2 shows entangled microfibers, 30, and crimped staple fibers, 31. The microfibers in particular entangle themselves with each other, with the staple fibers and with particles, 32, of polymeric gelling agent.

The composite web structures of the present invention can be made having a wide variety of properties depending upon the nature and the amounts of the web components employed, upon particular fiber orientation arrangements and upon the specific processing conditions utilized. For example, the absorbent web structures herein can be prepared having any desired basis weight. For use in disposable absorbent articles, dry basis weight of the web structures herein will preferably range from about 100 to 800 g/m², more preferably from bout 100 to 400 g/m². When such structures are to be used as absorbent cores for sanitary napkins, dry basis weight will generally range from about 200 to 450 g/m². When structures are to be used in infant diapers, dry basis weight will generally range from about 100 to 700 gm/m². For disposable training pants, dry basis weight will generally range from about 100 to 700 gm/m².

Caliper of the absorbent web structures herein can also be widely varied depending upon the desired end use of the structures. Frequently caliper of the dry web structure will range from about 0.46 to 3.1 centimeters, more preferably from about 1.5 to 2.1 centimeters. The preferred web structures of the present invention, by virtue of both their density and the properties of their selected types of components, do not significantly expand, i.e., increase in caliper, upon imbibing body fluids and similar electrolytes (under conditions of minimal confining pressure i.e., a confining pressure of 0.005 kPa). The preferred webs herein, in fact, may actually decrease in caliper upon fluid acquisition. These unique fluid absorption characteristics of the web structures herein may in part be responsible for the especially desirable comfort properties which preferred absorbent structures of the present invention possess.

At a constant basis weight, variations in web structure caliper result in variations in density of the structures herein. For these absorbent structures, such web density and caliper variations can influence comfort response, response to compression (i.e., bending ability and resilience), absorbent response (i.e., capacity, fluid uptake rate and fluid binding tenacity) and the ability to maintain body contact for fluid acquisition. Web density and caliper can be adjusted, for example, by varying the distance from the microfiber extruder outlet to the collector, by changing the microfiber/staple fiber ratio, by altering the amount of polymeric gelling agent employed, by changing the wind-up roll tension during web structure converting or by varying staple fiber denier and/or crimp level. The web structures of the present invention are those which have a dry density of from about 0.006 to 0.10 g/cm³, more preferably from about 0.006 to 0.04 g/cm³. For use as the absorbent core in sanitary napkin products, the web structures herein should generally have a density ranging from about 0.006 to 0.03 g/cm³. For use in infant diapers, the web structures herein will generally have a density ranging from about 0.01 to 0.04 gm/cm³. For use in disposable training pants, density of the structures herein will generally range from about 0.01 to 0.04 gm/cm³.

Dry density, for purposes of the present invention, is measured under a confining pressure of about 0.0007 psi (0.005 kPa). Density of such structures need not be uniform throughout the structure. Within the density ranges hereinbefore set forth, structures of this invention can contain regions of relatively higher or relatively lower density.

In addition to their behavior upon fluid acquisition, another important distinction between the composite web structures herein and similar absorbent structures of the prior art concerns the wet and dry resilience properties of the webs of this invention. Resilience involves the propensity of the composite web structures herein to recover their original dimensions after being compressed. As noted hereinbefore, preferred composite web structures of this invention are those which exhibit both wet and dry resilience properties that enable a given a three-dimensional composite web structure to recover to at least about 50%, and more preferably to at least about 65%, of its original transverse dimension after having been compressed to a transverse dimension which is 40% of its original transverse dimension. For purposes of this invention, such a determination of resilience can be made using a web structure of standard transverse dimension while embodying such a structure in a standard type of absorbent article chassis.

This standard chassis for determining web structure resilience is defined for purposes of this invention as the sanitary napkin of Example XX hereinafter set forth. The standard "original transverse dimension utilized is 6.35 cm (2.5 inches). Thus to determine resilience of the preferred composite web structures of this invention, web structure-containing sanitary pads of a given standard initial width (2.5 inches) can be compressed to the 60% strain level, i.e., to 1.0 inch in width, (40% of its original width), followed by removal of the compressive force to allow the sanitary pad to relax. Compressive force is applied for a period of three hours, followed by a relaxation period of 5 minutes. The final width of the pad is thereafter determined. Percent Resilience can then be calculated according to the equation:

$$\% \text{ Resilience} = \left[1 - \frac{(\text{Initial Width} - \text{Final Width})}{\text{Strain Level}}\right] \times 100$$

wherein Strain Level is the Initial pad width minus the Compressed Pad Width. The Percent Resilience according to this equation can be determined with the pads in either dry or wet condition.

The present invention also relates to disposable absorbent articles which utilize the absorbent composite structures herein as the fluid-absorbing "core" element. By "absorbent article" herein is meant a consumer product which is capable of absorbing significant quantities of water and other fluids (i.e., liquids), like body fluids. Examples of absorbent articles include disposable diapers, sanitary napkins, incontinence pads, disposable training pants, paper towels, facial tissues, and the like. These absorbent structures are particularly suitable for use in articles like sanitary napkins, diapers and incontinence pads.

Absorbent articles herein will frequently comprise a substantially liquid impervious backing sheet, a liquid pervious, relatively hydrophobic topsheet and an absorbent core comprising an absorbent structure of the present invention positioned between said backing sheet and said topsheet. Liquid impervious backing sheets can comprise any material, for example polyethylene or polypropylene having a caliper of about 1.5 mils, which will help retain fluid within the absorbent article. Relatively hydrophobic, liquid pervious topsheets can comprise any material such as polyester, polyolefin, rayon and the like which is substantially porous and permits a fluid to readily pass therethrough into the underlying absorbent core.

As indicated hereinbefore, the absorbency and comfort characteristics of the absorbent web structures herein render such structures especially suitable for use in sanitary napkins. Sanitary napkins (or in other terms, catamenial pads) utilizing the present absorbent structures may be derived from conventional sanitary napkins by simply replacing or supplementing the absorbent core thereof (typically a web of wood pulp fibers) with an absorbent composite structure of the present invention.

Figure 3:
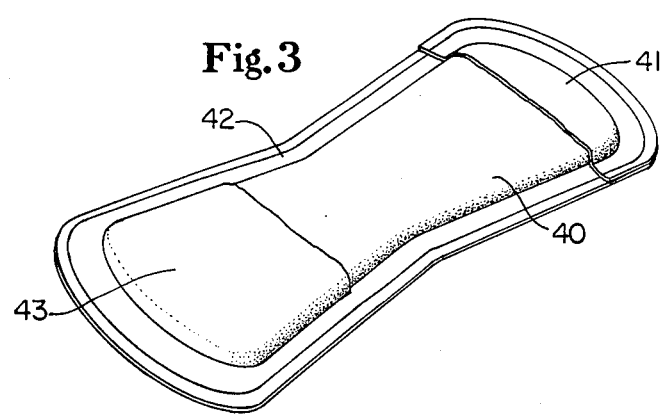
FIG. 3 represents a cut-away view of a sanitary napkin which employs a composite absorbent structure of this invention as an absorbent core.

An example of a sanitary napkin is shown in FIG. 3 of the drawings. This particular catamenial product comprises a pad, 40, of the absorbent composite structure of the present invention; a hydrophobic topsheet, 41; and a fluid impervious backsheet, 42. The topsheet and the backsheet are placed at opposite sides of the absorbent structure. Optionally, the absorbent structure is wrapped in envelope tissue, 43. Suitable materials for top sheets, bottom sheets and envelope tissue are well known in the art. A more detailed description of sanitary napkins and suitable materials for use therein is found in Duncan and Smith, U.S. Pat. No. 3,871,378, Issued Mar. 18, 1975; Mullane and Smith, U.S. Pat. No. 4,324,246, Issued Apr. 13, 1982 and Van Tillberg, U.S. Pat. No. 4,589,876, Issued May 20, 1986; the disclosures of which are incorporated herein by reference.

Figure 4:
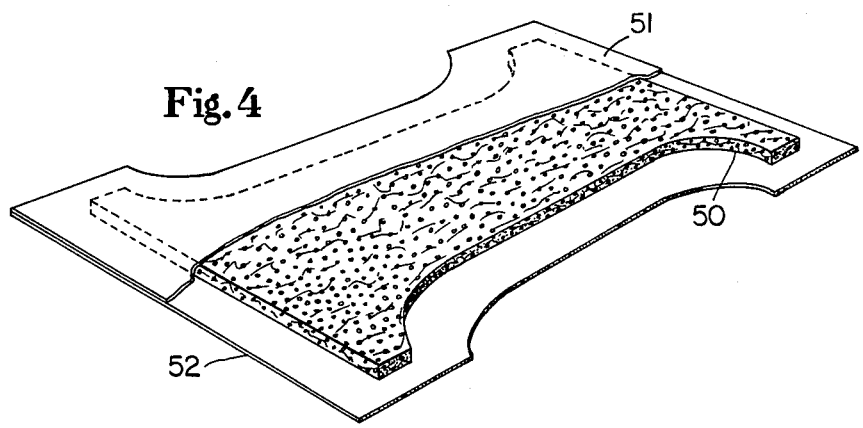
FIG. 4 represents a cut-away view of a disposable diaper which employs a composite absorbent structure of this invention as an absorbent core.

Other disposable absorbent articles which can employ the absorbent web structures herein are disposable diapers. Disposable diapers comprising the absorbent structures of the present invention may be made by using conventional diaper making techniques, but by replacing the wood pulp fiber web ("airfelt") core which is typically used in conventional diapers with an absorbent structure of the present invention. Composite structures of this invention may also be used in addition to conventional airfelt webs in disposable diapers. Articles in the form of disposable diapers are fully described in Duncan and Baker, U.s. Pat. No. Re. 26,151, Issued Jan. 31, 1967; Duncan, U.S. Pat. No. 3,592,194, Issued July 13, 1971; Duncan and Gellert, U.S. Pat. No. 3,489,148, Issued Jan. 13, 1970; and Buell, U.S. Pat. No. 3,860,003, Issued Jan. 14, 1975; which patents are incorporated herein by reference. A preferred disposable diaper for the purpose of this invention is illustrated by FIG. 4 of the drawings. Such a diaper includes an absorbent core, 50, comprising an absorbent composite structure of this invention; a topsheet, 51, superposed or co-extensive with one face of the core, and a liquid impervious backsheet, 52, superposed or co-extensive with the face of the core opposite the face covered by the topsheet. The backsheet most preferably has a width greater than that of the core thereby providing side marginal portions of the backsheet which extend beyond the core. The diaper is preferably constructed in an hourglass configuration.

Another preferred type of absorbent article which can utilize the absorbent structures of the present invention comprises training pants. Such training pants will generally include a non-woven, flexible substrate fashioned into a chassis in the form of briefs or shorts. An absorbent structure according to the present invention can then be affixed in the crotch area of such a chassis in order to serve as an absorbent "core." This absorbent core will frequently be over-wrapped with envelope tissue or other liquid pervious, non-woven material. Such core overwrapping thus serves as the "topsheet" for the training pants article.

The flexible substrate which forms the training pants chassis may comprise cloth or paper or other kinds of non-woven substrate and may be elasticized or otherwise stretchable. Leg bands or waist bands of such training pants articles may be elasticized in conventional fashion to improve fit of the article. Such a substrate will generally be rendered liquid impervious by treating or coating one surface thereof or by laminating the flexible substrate with another liquid impervious substrate to render the total chassis liquid impervious. In this instance, the chassis itself serves as the "backsheet" for the training pants article.

Figure 5:
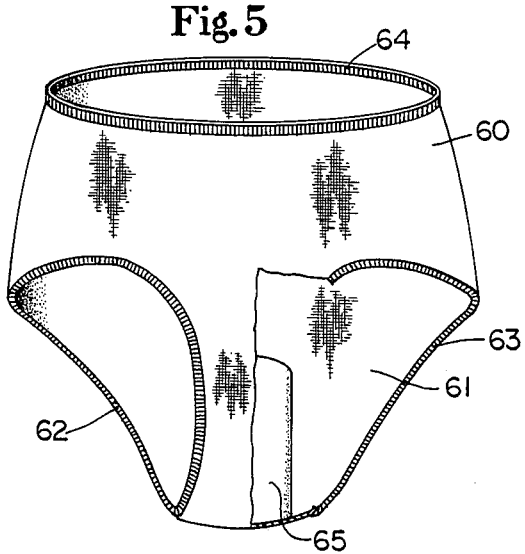
FIG. 5 represents a cut-away view of a disposable training pants product which employs a composite absorbent structure of this invention as an absorbent core.

A typical disposable training pants product is shown in FIG. 5 of the drawing. Such a product comprises an outer layer, 60, affixed to a lining layer, 61, by adhesion along the peripheral zones thereof. For example, the inner lining, 61, may be affixed to the outer layer, 60, along the periphery of leg band area, 62; along the periphery of leg band area, 63; and along the periphery of waistband area, 64. Affixed to the crotch area of the article is a generally rectangular absorbent core, 65, comprising an absorbent composite structure of the present invention. Typical training pants products of this kind are described in Roberts; U.S. Pat. No. 4,619,649; Issued Oct. 28, 1986, incorporated herein by reference.

TEST METHODS

In describing the present invention, characteristics of the staple fiber component such as water retention value and characteristics of the polymeric gelling agent such as gel volume are set forth. Where reported, these characteristics can be determined using the following test methods:

WATER RETENTION VALUE (WRV)

A sample of about 0.3 g to about 0.4 g of fibers is soaked in a covered container with about 100 ml distilled or deionized water at room temperature for between about 15 and about 20 hours. The soaked fibers are collected on a filter and transferred to an 80-mesh wire basket supported about 1¼ inches above a 60-mesh screened bottom of a centrifuge tube. The tube is covered with a plastic cover, and the sample is centrifuged at a relative centrifuge force of 1500 to 1700 gravities for 19 to 21 minutes. The centrifuged fibers are then removed from the basket and weighed. The weighed fibers are dried to a constant weight at 105° C. and reweighed. The water retention value is calculated as follows:

$$WRV = \frac{(W - D)}{D} \times 100$$

where,

W = wet weight of the centrifuged fibers;
D = dry weight of the fibers; and
W-D = weight of absorbed water.

GEL VOLUME IN ARTIFICIAL MENSES

Gel volume in artificial menses is determined as the weight (grams) of artificial menses which will be absorbed per gram of polymeric gelling agent. Such a determination is first made after two minutes of contact between gelling agent and artificial menses to give an indication of the speed with which the gelling agent takes up fluid. A determination is then made after an extended period (60 minutes) of contact between gelling agent and artificial menses in order to determine an equilibrium gel volume value.

Artificial menses employed in the gel volume comprises a mixture of sheep's blood and a synthetic mucous component. Each of these components and their preparation is described as follows:

---

I. Artificial Menses Components
A. Mucous
    31.0 g gastric mucin (ICN Biomedicals, Inc.)
    2.0 ml prepared lactic acid solution
    7.5 ml prepared potassium hydroxide solution
    450 ml prepared phosphate buffered saline solution
B. Blood
    500 ml sterile defibrinated sheep blood (Cleveland Scientific)

II. Preparation
A. Lactic Acid Solution
    1:10 dilution of 85-95% lactic acid:distilled water
B. Potassium Hydroxide Solution
    10% (by weight) potassium hydroxide in distilled water
C. Phosphate Buffered Saline Solution
  1. Solution A: 1.42 g anhydrous dibasic sodium phosphate
    8.50 g sodium chloride
    Add distilled water to a volume endpoint of 1 liter
  2. Solution B: 1.38 g hydrous monobasic sodium phosphate
    8.50 g sodium chloride
    Add distilled water to a volume endpoint of 1 liter
  3. Start with 450 ml of Solution A and add Solution B to raise the pH to an endpoint of 7.2.
D. Mucous Component
  1. Combine ingredients outlined in IA.
  2. Stir (and gently heat, if necessary) to solublize.
  3. Autoclave @ 121° C. for 15 minutes.
  4. Let solution cool.
E. Artificial Menses Fluid
  1. Mix the mucous and blood components together.
  2. Solution must be refrigerated and brought to room temperature before using.
  3. Use within seven days due to blood aging.

---

Using artificial menses prepared as indicated, gel volume values are determined by a procedure wherein particles of polymeric gelling agent (PGA), held in a paper "teabag", are soaked in artificial menses fluid and are then centrifuged to remove the fluid which has not been imbibed by the PGA particles. The equipment, procedure and calculations employed in such a procedure are described as follows:

A. Equipment
Sample holders -- glass cylinders (1.4 cm inside diameter, 3.4 height
Centrifuge tubes -- double chambered vessels wherein a first chamber is separated from the second chamber by a steel mesh seat for holding PGA-containing teabags
Teabag material -- cut to 5.0 cm × 8.0 cm rectangles
Balance -- 0.0001 g sensitivity range
Fluid bath -- 200 ml of swelling fluid in a 90 × 50 Pyrex crystallizing dish
Centrifuge -- Clinical model, with variable speed and a horizontal rotor with four 29.4 mm × 95 mm (I.D. X Depth) shields
Tachometer -- with adapter for measuring centrifuge speed
Drying beakers -- 10 ml volume B. Procedure
1. Teabags are inserted into sample holders and "Initial Teabag" weights are recorded.
2. Samples of PGA are weighed out to 0.0255 g ± 0.0005, and "Initial PGA" weights are recorded.
3. Samples are placed in an agitated fluid bath. Liquid is pipetted over the top of the PGA to insure fluid contact and to prevent gel blockage (teabag is also completely saturated with fluid).
4. Samples are equilibrated in the bath for one hour or two minutes, depending upon which type of gel volume measurement is being made.
5. Samples are then removed from the bath. Teabags containing PGA are carefully removed from the holders and placed in the centrifuge tubes.
6. Samples are centrifuged at 125 gravities (g's) force for 10 minutes. The 10 minute time does not include the time needed for the centrifuge to reach 125 g's (1 minute, depending on the centrifuged used).
7. Samples were removed from the centrifuge tubes and weighed. The "(Wet PGA + Wet Teabag)" weights are recorded.

C. Calculations
Gel Volume can be expressed as the weight fraction of the amount of swelling fluid absorbed to the initial weight of PGA. Gel volume is defined as follows relative to experimentally measured and calculated parameters.

Gel Volume - Centrifugation:
The Gel Volume - Centrifugation (GVC) is calculated with the following equation:

$$GVC = \frac{\text{Wet } PGA - \text{Initial } PGA}{\text{Initial } PGA}$$

where the Initial PGA is the PGA sample weighed in Procedure Step #2, and the Wet PGA is the swelled PGA sample after centrifugation. The WET PGA (WPGA) is calculated using:

$$WPGA = [(WPGA + WTB) - WTB]$$

where (WPGA + WTB) is the quantity weighed in Procedure Step #7, and WTB is the Wet Teabag. Since the wet teabag also includes some solids from the fluid, WTB is calculated using:

$$WTB = (ITB)(WTB \text{ factor})$$

where ITB is the Initial Teabag weight in Procedure Step #1, and the WTB factor is obtained from a calibration curve. The WTB curve for artificial menses is generated by the following equation for centrifugal force values within the ranges of 120 to 302 g's. WTB Factor = [−0.00109 × Centrifugal Force (g's)] + 1.85127

GEL VOLUME IN SYNTHETIC URINE

Gel volume in terms of grams of synthetic urine absorbed per gram of polymeric gelling agent is determined by swelling the polymer samples in several aliquots of synthetic urine. The amount of such synthetic urine actually absorbed by the polymeric gelling agent is determined by a procedure which involves use of a synthetic urine solution containing Blue Dextrin so that optical absorbence measurements can be used to caculate the amount of synthetic urine that is not taken up by the hydrogel which forms.

(a) Blue Dextrin Solution Preparation

A 0.03% Blue Dextrin (BD) solution is prepared by dissolving 0.3 parts of Blue Dextrin (Sigma D-5751) in 1000 parts of Synthetic Urine (SU) solution. Synthetic Urine is 15.0 parts of 1% Triton X-100 ®, 60.0 parts of NaCl, 1.8 parts of $CaCl_2.2H_2O$, and 3.6 parts of $MgCl_2.6H_2O$, diluted to 6000 parts with distilled $H_2O$. The resulting solution has an absorbence of about 0.25 at its absorbence maximum of 617 nm.

(b) Hydrogen Equilibration

Aliquots of the hydrogen-forming polymeric gelling agent to be tested are swelled in (i) 20 parts of Synthetic Urine (SU) solution and (ii) 20 parts of Blue Dextrin (BD) solution. The suspension in the Blue Dextrin (BD) solution is prepared in duplicate. For most hydrogels, 0.1–0.25 parts of hydrogel-forming dried powder is required to give a sufficiently high spectrophotometer reading relative to the Blue Dextrin reference solution. One hour of equilibration at ambient temperature under gentle stir-bar stirring is sufficient for swelling equilibrium to be attained. After equilibration, a 3 ml aliquot of supernatant is separated from each gel suspension by decantation followed by centrifugation. Two minute gel volume readings can be obtained by swelling the polymeric gelling agent for only two minutes.

(c) Gel Volume Determination

The optical absorbency (ABS) of each supernatant is determined spectrophotometrically with an accuracy of 0.001 absorbence units. The Synthetic Urine solution is used as an ABS=0.0 reference. The absorbency of the supernatant from the synthetic urine suspension without Blue Dextrin should not exceed 0.01A; higher values indicate scattering from residual hydrogel gel particles or residual additives, and further centrifugation is necessary. The absorbency of the Blue Dextrin supernatants should exceed the absorbency of the Blue Dextrin reference solution by at least 0.1 absorbence units. Absorbency values below this range indicate the need to adjust the amount of polmeric gelling agent used to prepare the gel suspension.

(d) Gel Volume Calculation

The Gel Volume is synthetic urine of the polymeric gelling agent in gms/gm is calculated from (i) the weight fraction of the polymeric gelling agent in the gel suspension and (ii) the ratio of the excluded volume to the total volume of the suspension. Since Blue Dextrin is excluded from the hydrogel due to its high molecular weight, this ratio is related to the measured absorbencies. The following equation is used to calculate the gel volume:

$$\text{Gel Volume} = \left[ \frac{(\text{gms } BD \text{ Solution})}{(\text{gms polymeric gelling agent}^*)} \right] \times \left[ 1 - \frac{(ABS\ BD \text{ solution})}{(ABS\ BD \text{ supernatant} - ABS\ SU \text{ supernatant})} \right]$$

*Corrected to a dry weight basis

The absorbent web structures herein, as well as disposable absorbent articles containing them are illustrated by the following examples. In these examples, reported density measurements are all made under a confining pressure of 0.0007 psi (0.005 kPa). Furthermore ± values where reported indicate deviation at the 95% confidence level.

EXAMPLE I

Two composite absorbent structures are prepared from polypropylene microfibers, crimped polyethelene terephthalate (PET) staple fibers, particles of polymeric gelling agent, and nonionic surfactant as a hydrophilizing agent. A more complete description of each of these components is given as follows:

---

Polypropylene Blown Microfibers (BMF)

Size = 5 microns in diameter (average)
Fiber Material Modulus = At least $0.9 \times 10^{10}$ dynes/cm$^2$ Staple Fibers Type = Kodel ® PET marketed by Eastman
Size = 15 denier
Water Retention Value = 5%
Percent Crimp = 40%
Fiber Material Modulus = $3.0 \times 10^{10}$ dynes/cm$^2$ Polymeric Gelling Agent (PGA)

Type = Polyacrylate - Waterlok J-550 ® marketed by Grain Processing Corp.
Size = less than 300 microns (avg.)
Equilibrium Gel Volume (Artificial Menses) = 35.8 g/g.
Two Minute Gel Volume (Artificial Menses) = 30.7 g/g.

Hydrophilizing Agent

Type = Triton GR-5M ® anionic surfactant marketed by Rohm & Haas

---

To prepare both structures, PET staple fiber and polymeric gelling agent are admixed together and introduced into a stream of microfibers using an apparatus similar to that shown in the drawing hereinbefore described. The composite web structures which are prepared have the characteristics shown in Table I.

TABLE I

Absorbent Web Structures: Variation in BMF:PET Staple Fiber Ratio
Surfactant treatment: Triton GR-5M ® @ 1.0% by weight (target) of polypropylene fibers.

| Sample Number | BMF: Staple Ratio | Target PGA Level (wt. %) | Component Basis Weight (g/m$^2$) | | | Total Composite Basis Weight (g/m$^2$) |
| | | | PGA | BMF | 15-den PET Staple | |
|---|---|---|---|---|---|---|
| 1 | 30:70 | 30 | 81 | 57 | 133 | 271 |
| 2 | 70:30 | 30 | 81 | 133 | 57 | 271 |

These absorbent structures are prepared under conditions such that Sample #1 has a density of about 0.016 gm/cm$^3$ and Sample #2 has a density of about 0.022 gm/cm$^3$.

EXAMPLES II–XII

A number of composite structures similar to that of Example I are prepared but with varying levels and types of polymeric gelling agents. In addition to J-

550®, other polymeric gelling agents (PGAs) utilized in such structures include SANWET IM-1000®, a starch acrylate material marketed by Sanyo Chemical Company and AQUALIC®, a polyacrylate material marketed by Nippon Shokubai KK. A description of these composite structures is set forth in Table II. The webs in Table II range in density from about 0.008 gm/cm³ to about 0.023 gm/cm³.

TABLE II

Absorbent Web Structures: PGA Type and Level Variations
Surfactant treatment: Triton GR-5M ® @ 1.0% by weight (target) of polypropylene fibers.

| Example Number | PGA Type | Target PGA Level (wt. %) | Component Basis Weight (g/m²) | | | Total Composite Basis Weight (g/m²) |
|---|---|---|---|---|---|---|
| | | | PGA | Micro- fi- ber | 15-den PET Sta- ple | |
| II | J-550® | 25 | 62.5 | 62.5 | 125 | 250 |
| III | J-550® | 40 | 125.0 | 62.5 | 125 | 312.5 |
| IV | J-550® | 15 | 33.1 | 62.5 | 125 | 220.6 |
| V | Sanwet®* | 7 | 14.1 | 62.5 | 125 | 201.6 |
| VI | Sanwet® | 15 | 33.1 | 62.5 | 125 | 220.6 |
| VII | Sanwet® | 20 | 50.0 | 75.0 | 125 | 250 |
| VIII | Sanwet® | 40 | 125.0 | 62.5 | 125 | 312.5 |
| IX | Aqualic®** | 7 | 14.1 | 62.5 | 125 | 201.6 |
| X | Aqualic® | 15 | 33.1 | 62.5 | 125 | 220.6 |
| XI | Aqualic® | 30 | 80.4 | 62.5 | 125 | 267.9 |
| XII | Aqualic® | 40 | 125.0 | 62.5 | 125 | 312.5 |

*Equilibrium Gel Volume (artificial menses) = 47.1 g/g Two-minute Gel Volume = 19.4 g/g
**Equilibrium Gel Volume (artificial menses) = 28.9 g/g Two Minute Gel Volume = 18.6 g/g

EXAMPLES XIII-XIX

A number of composite structures similar to that of Example I are prepared but with varying types of staple fiber and staple fiber denier. A description of these articles is set forth in Table III.

TABLE III

Absorbent Web Structures: Variation in Staple Type and Denier
Surfactant treatment: Triton GR-5M ® @ 1.0% by weight (target) of polypropylene fibers
Composite Basis Weight (g/m²)

| Example Number | Staple Fiber Type/ Denier | PET Staple | Other Staple | Polypropylene BMF | J-550® PGA | Total Composite Basis Weight (g/m²) | Composite Density (g/cm³) |
|---|---|---|---|---|---|---|---|
| Variation in Staple Type | | | | | | | |
| XIII | PET/15den | 125 | — | 62 | 80 | 267 | 0.012 |
| XIV | PET/15den Cotton | 93 | 32 | 62 | 80 | 267 | 0.013 |
| XV | Cotton | — | 100 | 62 | 80 | 242 | 0.012 |
| XVI | PET/15den Rayon | 32 | 93 | 62 | 80 | 267 | 0.016 |
| XVII | Rayon | — | 125 | 62 | 80 | 267 | 0.024 |
| XVIII | PET/50den | 125 | — | 62 | 62 | 249 | 0.018 |
| XIX | PET/5den | 57 | — | 133 | 81 | 271 | 0.023 |

Examples XIII, XVIII and XIX are web structures of the present invention. Examples XIV-XVII are comparative examples containing staple fibers of the type typically used in prior art microfiberbased webs but not of the type contemplated for use in the structures of the present invention.

EXAMPLE XX

A sanitary napkin employing an absorbent structure of this invention is prepared as follows:
a composite absorbent structure is prepared in the general manner described in Example I, having a caliper of about 1.8 cm and a density of about 0.016 g/cm³ as measured under a confining pressure of 0.0007 PSI (about 49N/m²). This structure is cut into a rectangular web of 7 in.×2.5 in. (about 18 cm×6.4 cm). This web is placed against a waterproof backing sheet (9 in.×3 in.) of embossed polyethylene having an embossed caliper of about 2.4 mils. The web and backsheet are wrapped in a formed film polyethylene (Dri-Weave®) having a caliper of about 17.2 mils. The web is bonded to the topsheet with a 0.001 in. film of water soluble adhesive. The ends of the resulting sanitary napkin are heat sealed and tapered. A 7 in.×1.5 in. strip of adhesive is placed on the underside of the sanitary napkin and covered with a 8 in.×2 in. piece of release paper. The top side of the sanitary napkin is sprayed with 0.01 g of a nonionic surfactant. The resultant absorbent article is useful as a sanitary napkin having especially desirable comfort and absorbent properties.

EXAMPLE XXI

The resilient characteristics of sanitary napkins prepared as generally described in Example XX (without the underside adhesive/release paper combination) can be demonstrated by the testing procedures hereinbefore described which involve edgewise compression of such products followed by removal of the compressive force to allow the sanitary pad to relax. Thus sanitary pads of a given standard initial width (i.e., 2.5 inches) are compressed in the cross direction to the 60% strain level (i.e., a width of 1.0 inch or 40% of the initial width) for a period of three hours. The compressive force is then removed, and after a relaxation period of five minutes, the final width of the pad is measured. A percent resilience is then calculated using the equation hereinbefore set forth. For Example XX pads having an initial width of 2.5 inches and a 1.5 inch strain level, percent resilience is calculated as follows:

$$\% \text{ Resilience} = \left[1 - \frac{(2.5 - \text{Final Width})}{1.5}\right] \times 100$$

wherein Final Width is measured in inches. The % Resilience values can be measured for sanitary napkins in both the wet (e.g., containing 5 ml of artificial menses) and dry states.

Using the foregoing procedures, % resilience values are calculated for sanitary napkins of the general Examples XX type having different kinds of absorbent cores.

Results are shown in Table IV wherein the effect of staple fiber type on sanitary pad resilience is shown.

TABLE IVA

Effect of Core Composition on Sanitary Pad Resilience
Surfactant treatment: Triton GR-5M ® @ 1.0% by weight (target) of polypropylene fibers

| Example Number | Core Composition* | Dry Resilience (% of strain recovered) | | Wet Resilience (% of strain recovered) | |
|---|---|---|---|---|---|
| — | 100% Fluff | 66.4 | ±7.0 | 27.5 | ±4.5 |
| II | 33 BMF: 67 PET-15den with 25% J-550 ® | 97.4 | ±4.5 | 84.2 | ±8.1 |

TABLE IVB

Effect of Staple Fiber Type on Sanitary Pad Resilience
Surfactant treatment: Triton GR-5M ® @ 1.0% by weight (target) polypropylene fibers

| Example Number | Core Composition* | Wet Resilience (% of strain recovered) | |
|---|---|---|---|
| II | 33 BMF: 67 PET-15den: with 25% J-550 ® | 84.2 | ±8.1 |
| XIV (Comparative) | 33 BMF: 50 PET-15den: 17 Cotton with 30% J-550 ® | 58.0 | ±7.3 |
| XV (Comparative) | 38 BMF: 62 Cotton with 30% J-550 ® | 34.9 | ±22 |
| XVI (Comparative) | 33 BMF: 17 PET-15den: 50 Rayon with 30% J-550 ® | 52.9 | ±10 |

*Given as weight ratios of the fiber material with wt % of composite for the PGA component.

The Table IVA data show that sanitary pads prepared from absorbent structures of the invention (e.g., as embodied by Example II) possess desirable anti-bunching or resilience properties relative to pads prepared with absorbent structures containing cellulose fluff fibers. While the fluff core displays poor dry resilience, it is especially deficient when tested in a wet state. On the other hand, the microfiber composite core shows minimal difference between dry and wet resilience. This is hypothesized to be due primarily to the function of the relatively stiff PE staple fibers, which are essentially nonabsorbent and do not undergo a significant dry to wet modulus change.

The Table IVB data show that partial or whole substitution of a long cellulosic fiber such as cotton for the PET staple results in a significant reduction in wet core resilience (relative to a microfiber composite core containing only PET as the staple fiber). Data are also presented in Table IV-B for a microfiber composite core that contains both PET and Rayon as the staple fiber component. As with introduction of cotton fibers, long rayon fibers introduced into the web result in a reduction in wet resilience relative to the composite containing only PET as the staple fiber.

EXAMPLE XXII

This example provides data to demonstrate the effect of BMF:staple ratio, and the staple fiber denier on the resilience of sanitary pads made from absorbent structures of this invention. In general, the effect of change in BMF:staple ratio from 33:67 to 70:30 (at a staple denier of 15), and of change in staple denier from 15 to 50 is small compared to the difference between microfiber composite resilience and that of fluff structures. These results are set forth in Table V.

TABLE V

Effect of BMF:Staple Ratio on Resilience
and
Effect of Staple Fiber Denier on Resilience

| Example Number | Matrix Composition* | Dry Resilience (% of strain recovered) | | Wet Resilience (% of strain recovered) | |
|---|---|---|---|---|---|
| — | 100% Fluff | 66.4 | ±7.0 | 27.5 | ±4.5 |
| II | 33 BMF: 67 PET-15den with 25% J-550 ® | 97.4 | ±4.5 | 84.2 | ±8.1 |
| I(2) | 70 BMF: 30 PET-15den with 30% J-550 ® | 91.0 | ±0.7 | 74.9 | ±6.5 |
| XVIII | 33 BMF: 67 PET-50den with 25% J-550 ® | 90.8 | ±2.4 | 69.3 | ±7.9 |

*Given as weight ratios of the fiber materials with wt. % of composite for the PGA component.

EXAMPLE XXIII

This example shows the effect of BMF to staple ratio and staple denier on resilience properties of sanitary napkins containing microfiber-based absorbent cores. A number of composite structures similar to that of Example I are prepared with variations in ratios of BMF to Staple fiber and staple fiber deniers. Since with respect to resilience properties (evaluated hereinafter) the PGA component plays only a minimal role, the polymeric gelling agent component is omitted from those structures. These various structures are described in Table VI.

TABLE VI

Absorbent Web Structures: Variation in BMF:Staple Ratio and Staple Denier
Surfactant treatment: Triton GR-5M ® @ 1.0% by weight (target) of polypropylene fibers (no PGA component)

| Sample Number | BMF: Staple Ratio | PET Staple Denier | Component Basis Weight (g/m$^2$) | | Total Composite Basis Weight (g/m$^2$) | Composite Density (g/cm$^3$) |
|---|---|---|---|---|---|---|
| | | | BMF | 15-den PET Staple | | |
| A | 30:70 | 5 | 60 | 140 | 200 | 0.008 |
| B | 50:50 | 5 | 100 | 100 | 200 | 0.010 |
| C | 70:30 | 5 | 140 | 60 | 200 | 0.011 |
| D | 30:70 | 15 | 60 | 140 | 200 | 0.008 |
| E | 50:50 | 15 | 100 | 100 | 200 | 0.010 |
| F | 70:30 | 15 | 140 | 60 | 200 | 0.013 |
| G | 30:70 | 50 | 60 | 140 | 200 | 0.007 |
| H | 50:50 | 50 | 100 | 100 | 200 | 0.007 |
| I | 70:30 | 50 | 140 | 60 | 200 | 0.010 |

Web structures of the Table VI type are tested for their resilience properties using the general procedures described in Example XXI. Except where noted, resilience measurements are made on the webs per se and not on sanitary napkins containing the webs as cores. Results are set forth in Table VII.

TABLE VII

Effect of BMF:Staple Ratio on Resilience (No PGA)
and
Effect of Staple Fiber Denier on Resilience (No PGA)

| TABLE VI Sample Number | Web Composition (wt. %) | Dry Resilience (% of strain recovered) | Wet Resilience (% of strain recovered) |
|---|---|---|---|
| | **100% Fluff | 66.4 ±7.0 | 27.5 ±4.5 |
| A | 30% BMF 70% PET-5den | 94.8 ±4.2 | N/A* |
| B | 50% BMF 50% PET-5den | 94.5 ±3.2 | N/A |
| C | 70% BMF 30% PET-5den | 97.4 ±2.6 | N/A |
| D | 30% BMF 70% PET-15den | 88.9 ±2.9 | N/A |
| E | **50% BMF 50% PET-15den | 92.3 ±2.4 | 84.2 ±4.1 |
| F | 70% BMF 30% PET-15den | 88.4 ±1.9 | N/A |
| G | 30% BMF 70% PET-50den | 93.1 ±2.9 | N/A |
| H | 50% BMF 50% PET-50den | 92.5 ±1.9 | N/A |
| I | 70% BMF 30% PET-50den | 95.6 ±4.5 | N/A |

*Not Available
**These two webs are tested as cores in Example XX type sanitary napkins.

The Table VII data indicate the effect of BMF:staple ratio on dry resilience for structures similar to those of the present invention but which contain no polymeric gelling agent. PGA has only minimal effect on resilience properties of such structures (within the limits of this invention and for the test procedures used.) Therefore, trends indicated by the Table VII data should be applicable to structures of similar fibrous composition but with PGA included.

The Table VII data indicate that there is no effect of BMF:staple ratio or staple denier on dry resilience over the ranges tested, i.e., BMF:staple ratios of 30:70 to 70:30, and PET staple deniers of 5 to 50. All of the microfiber-containing structures set forth in Table VI provide sanitary napkins which exhibit significantly higher resilience than does the napkin with the fluff core.

EXAMPLE XXIV

Absorbent structures of the invention also possess desirable flexibility characteristics relative to conventional fluff core structures. Flexibility can be defined as the amount of resistance a material offers to deformation. It can be quantified through force (resistance) measurement as a function of strain during edgewise compression.

The flexibility characteristics of several structures of the present invention are compared with those of a conventional 100% fluff absorbent core from a commonly marketed sanitary napkin (ALWAYS-). Such characteristics are demonstrated by measuring resistance force as a function of % strain during edgewise compression of the absorbent structure while the structure is embodied in a sanitary napkin chassis in the manner described in Example XXI. The % strain value is defined as follows:

$$\% \text{ Strain} = \frac{(\text{Initial Pad Width} - \text{Compressed Pad Width})}{\text{Initial Pad Width}} \times 100$$

Data showing this resistance force/percent strain relationship is set forth in Table VIII and is depicted graphically in FIGS. 6 and 7. These measurements are made on the absorbent structures both when they are dry and when they have been loaded with 25 ml of artificial menses.

TABLE VIII

| Structure | % Strain | Dry Resistance Force(g) | % Strain | Wet Resistance Force |
|---|---|---|---|---|
| 100% Fluff | 11 | 351 | 11 | 369 |
| | 30 | 526 | 30 | 439 |
| | 50 | 1436 | 50 | 901 |
| Example I(2) | 11 | 92 | 11 | 105 |
| | 31 | 105 | 31 | 91 |
| | 49 | 169 | 49 | 164 |
| Example II | 11 | 80 | 11 | 107 |
| | 31 | 76 | 31 | 115 |
| | 49 | 122 | 49 | 163 |
| Example XVIII | 11 | 86 | 11 | 100 |
| | 31 | 83 | 31 | 91 |
| | 49 | 140 | 49 | 163 |

The data set forth in Table VIII depicted graphically in FIG. 6 indicate that absorbent structures of the present invention (spanning a range of compositions as indicated by the Examples cited) are dramatically more flexible than a conventional 100% fluff core. The property of core flexibility if hypothesized to have important impact on consumer comfort perception during sanitary pad use. The fluff core generates two to five times more resistance to compression than the microfiber composite core, depending on the stain level. This translates to greatly reduced wearer awareness of microfiber composite structures during menstrual use.

Importantly, the flexibility advantage of microfiber composite cores versus fluff is the same whether the flexibility is measured in the dry or wet state. Up to 25 ml artificial menses fluid floodings have no significant impact on measured flexibility for either microfiber composite or fluff structures. FIG. 7 shows the flexibility response of fluff and microfiber composite absorbent structures after having loaded the cores with 24 ml of artificial menses.

EXAMPLE XXV

Preferred absorbent structures of the present invention possess unique properties upon wetting of the structures with either menses or urine inasmuch as such structures actually decrease in caliper upon wetting. This phenomenon is illustrated by the data presented in Tables IX and X showing structure caliper as a function of increasing fluid loading under a confining pressure of 0.0007 psi.

TABLE IX

| Structure | Fluid | Loading(ml) | Caliper (inches) | % Caliper Loss |
|---|---|---|---|---|
| Example III 20% BMF 40% PET 40% J-550 ® | Artificial Menses | 0 | 0.75 | 0 |
| | | 15 | 0.62 | 17 |
| | | 35 | 0.57 | 24 |
| | | 55 | 0.54 | 27 |
| | | 75 | 0.55 | 26 |
| | | 95 | 0.57 | 24 |
| | | 115 | 0.57 | 24 |
| | | 145 | 0.59 | 21 |

TABLE X

| Structure | Fluid | Loading(ml) | Caliper (inches) | % Caliper Loss |
|---|---|---|---|---|
| Example II | Synthetic | 0 | 0.74 | 0 |

TABLE X-continued

| Structure | Fluid | Loading(ml) | Caliper (inches) | % Caliper Loss |
|---|---|---|---|---|
| 25% BMF | Urine | 5 | 0.68 | 8 |
| 50% PET | | 25 | 0.63 | 15 |
| 25% J-550 ® | | 45 | 0.59 | 20 |

The Table IX data show that the absorbent structure described in Example III (with 40% J-550® PGA) collapses about 24% as it is saturated with artificial menses. The Table X data show that the absorbent structure of Example II (with 25% J-550® PGA) collapses about 19% as it is loaded with synthetic urine.

EXAMPLE XXVI

The comfort properties of sanitary napkins prepared using the absorbent structures of the present invention are further demonstrated by consumer panel testing wherein panelists actually wear the products being evaluated. Panels are conducted as paired comparisons of two products (alternately wearing one pad, then the other) in either a "menstrual-use" (panelists wear pads according to own habits during menstruation) or "dry-wear" format (panelists wear one pad of each kind for three hours each, then fill out questionnaire). Comfort data are based on panelist response to a direct question about which pad was preferred for comfort. One point is counted when there is a preference for one pad over the other, while one half a point is counted for each pad when there is no preference. Final comfort data is presented as the percent of total possible points for each pad.

Pairs of products tested in this manner include 1) a conventional commercial sanitary pad (ALWAYS®) having a 100% cellulose fluff core and 2) a sanitary pad employing a microfiber-containing structure of the present invention as an absorbent core along with a 2.5"×2.5" core insert positioned as an auxiliary core in the center of the product. All products tested are prepared as generally described in Example XX.

A description of the products tested and the panel test results are set forth in Table XI.

TABLE XI

Comfort Properties: Consumer Panel Data

| Example Number | Product Core Type | Chassis Design | Panel Type | Comfort Preference |
|---|---|---|---|---|
| VII | Microfiber/Staple PGA | Tubular* | Menstrual | 75 |
| — | ALWAYS ® Maxi (Fluff) | Tubular | Menstrual | 25 |
| XXIII(D) | Microfiber/Staple | Tubular* | Dry Wear | 78 |
| — | ALWAYS ® Maxi (Fluff) | Tubular | Dry Wear | 22 |

*As described in Example XX, but with a 2.5" × 2.5" core insert also included.

Data in Table XI show that prototype products containing structures of the present invention are preferred by panelists 3 to 1 for comfort over ALWAYS® maxi pads (with a fluff core).

EXAMPLE XXVII

Absorbent performance of the microfiber-based structures of the present invention can be demonstrated by actual menstrual-use testing and by laboratory absorption testing. For actual in use tests panelists wear either a conventional commercially available sanitary napkin (ALWAYS® or shaped ALWAYS® with wings) or a sanitary napkin prepared using an absorbent structure of the present invention. Upon completion of the tests, panelists report instances of panty soiling associated with the wearing of the product.

A description of the products employed, as well as test results, are set forth in Table XII:

TABLE XII

Absorbent Performance Data: Consumer Panel Results

| Example Number | Product Core Type | Chassis Design | Panel Type | % Soiling* (% of worn pads) |
|---|---|---|---|---|
| III | BMF/Staple/PGA | Tubular** | Menstrual | 59 |
| II | BMF/Staple/PGA | Tubular** | Menstrual | 60 |
| XVIII | BMF/Staple/PGA | Tubular** | Menstrual | 49 |
| — | ALWAYS ® Maxi (Fluff) | Tubular | Menstrual | 66 |
| I(2) | BMF/Staple/PGA | Shaped, Wings | Menstrual | 31 |
| — | Fluff*** | Shaped, Wings | Menstrual | 31 |

*% Soiling: used pads are returned with panty attached - soiling is defined as any visual incidence of menses on the panties.
**As described in Example XX, but with 2.5" × 2.5" core insert also included.
***Basis Weight = 465 gm/m².

The Table XII data indicate that sanitary pads using the microfiber-based absorbent cores of the present invention provide soiling protection that is equivalent to that provided by an all-fluff product when tested in either the tubular or "shaped with wings" chassis design.

EXAMPLE XXVIII

Absorbent capacity of the microfiber-based absorbent structures of the present invention can also be demonstrated by a zero head capillary sorption test. In such testing, samples of absorbent structures are placed on a 6 cm diameter glass frit [Por E (ASTM 4-8 microns) from Ace Glass] and is maintained in contact with a reservoir containing synthetic urine. The height of the frit and height of the reservoir are adjusted to the same level. A confining weight of 0.5 psi is placed on top of the structure sample. Using this setup, the number of grams of fluid taken up per gram of structure at equilibrium can be determined.

Capillary sorption data for special types of absorbent structures are set forth in Table XIII.

TABLE XIII

Absorbent Performance Data: Capillary Sorption Testing
Test Fluid: Synthetic Urine
Confining Weight: 0.5 psi

| Example Number | Core Material | Capacity (g/g) |
|---|---|---|
| XXIII(D) | BMF/Staple only | 9.7 ± 0.2 |
| I(1) | BMF/Staple/PGA | 11.5 ± 0.2 |
| — | Fluff | 7.3 ± 0.5 |

The Table XIII data show that the structures of the present invention have a higher absorbent capacity than that of fluff. This is due to the relatively low density (high void volume) of the cores of this invention. It should be noted that PGA increases the absorbent capacity of the structures herein.

EXAMPLE XXIX

A diaper is prepared as described in U.S. Pat. No. 3,860,003, Buell, issued Jan. 14, 1975, incorporated herein by reference, except that, in place of the absorbent diaper core disclosed therein (e.g., made from air-laid wood pulp) there is utilized as a core inserted between the top sheet and the backsheet an hourglass-shaped absorbent structure of the present invention. The absorbent structure is made as described in Table I, Sample 2. The basis weight is 680 gm/m²; the density is 0.022 gm/cm³, resulting in a core thickness of 30.9 mm, measured at a confining pressure of 0.0007 psi.

EXAMPLE XXX

Absorbent structures of the present invention are made with polypropylene microfibers, PET staple fibers and acrylic acid grafted starch hydrogel having a weight average particle size of about 25 microns ("SANWET IM 1000 ®", from Sanyo Co, Japan) using the process of Example I. The absorbent structures have a basis weight of 680 gm/m²) and a caliper of 3.09 cm which corresponds to a density of 0.022 gm/cm³. The structures are covered with a sheet of envelope tissue, and cut to a size of 3.5 in.×15.5 in. (about 9×40 cm).

Absorbent structures of this type are then used as inserts in diaper products prepared as described in U.S. Patent 3,860,003, Buell, issued Jan. 14, 1975, incorporated herein by reference. The hourglass-shaped soft wood pulp cores of the diapers have the following dimensions: length: 15.5 in. (about 40 cm), width at the ears: 10.5 in. (about 27 cm), and width in the center: 3.75 in. (about 9.5 cm). The absorbent structures of this invention are inserted lengthwise into the above-described diapers, in between the hourglass-shaped core and the polyethylene backing sheet, the envelope tissue against the hourglass-shaped core.

Such inserts improve the absorbent capacity of these diapers for urine.

What is claimed is:

1. An absorbent composite structure suitable for use in disposable absorbent articles of improved comfort, integrity and absorbency characteristics, said composite structure comprising
   (A) from about 10% to 85% by weight of the composite of blown microfibers, substantially all of which are of a diameter less than about 50 microns, said microfibers being formed from synthetic polymeric material having a modulus value when dry of at least about $0.1 \times 10^{10}$ dynes/cm², said modulus value not diminishing significantly when said microfibers are wet;
   (B) from about 10% to 85% by weight of the composite of substantially non-absorbent synthetic staple fibers, substantially all of which have a denier of from about 5 to 70 and a percent crimp of at least about 15%, said staple fibers being formed from a synthetic polymeric material having a modulus value when dry of at least about $0.1 \times 10^{10}$ dynes/cm², said modulus value not diminishing significantly when said staple fibers are wet;
   (C) from about 5% to 60% by weight of the composite of particles of a polymeric gelling agent having an equilibrium gel volume of at least about 20 grams of artificial menses per gram of gelling agent, a two-minute gel volume which is at least 40% of the equilibrium gel volume, and an extractable polymer content in synthetic urine of no more than about 17% by weight, substantially all of said particles ranging in diameter from about 30 microns to 2 mm; and
   (D) from about 0.01% to 10% by weight of the composite of a hydrophilizing agent which serves to hydrophilize the microfiber and staple fiber components;

said hydrophilized microfibers, table fibers and polymeric gelling agent particles being combined in a manner which forms a composite web having a dry density of from about 0.006 to 0.10 g/cm³.

2. An absorbent composite structure suitable for use in disposable absorbent articles of improved comfort, integrity and absorbency characteristics, said composite structure comprising
   (A) from about 10% to 85% by weight of the composite of blown microfibers, substantially all of which are of a diameter less than about 50 microns, said microfibers being formed from synthetic polymeric material selected from polyolefins, polyesters, polyamides; polystyrenes and polyacrylics;
   (B) from about 10% to 85% by weight of the composite of substantially non-absorbent synthetic staple fibers, substantially all of which have a denier of from about 5 to 70 an a percent crimp of at least about 15%, said staple fibers being formed from a synthetic polymeric material selected from polyolefins, polyesters, polyacrylics, polyamides and polystyrenes;
   (C) from about 5% to 60% by weight of the composite of particles of a polymeric gelling agent having an equilibrium gel volume of at least about 20 grams of artificial menses per gram of gelling agent, a two-minute gel volume which is at least 40% of the equilibrium gel volume, and an extractable polymer content in synthetic urine of no more than about 17% by weight, substantially all of said particles ranging in diameter from about 30 microns to 2 mm; and
   (D) from about 0.01% to 10% by weight of the composite of a hydrophilizing agent which serves to hydrophilize the microfiber and staple fiber components;

said hydrophilized microfibers, staple fibers and polymeric gelling agent particles being combined in a manner which forms a composite web having longitudinal, traverse and thickness dimensions, said composite web having a dry density of from about 0.006 to 0.10 g/cm³, with said composite web further exhibiting both wet and dry resilience properties which enable such a composite web to recover to at least 50% of its original transverse dimension after compression to a transverse dimension which is 50% of its original transverse dimension.

3. An absorbent composite structure according to claim 2 wherein
   (A) the polymeric gelling agent has an equilibrium gel volume of at least about 25 grams of artificial menses per gram of polymeric gelling agent, a two minute gel volume which is at least 50% of the equilibrium gel volume, and an extractable polymer content in synthetic urine of no more than 10% by weight and comprises polymers selected from hydrolyzed acrylonitrile grafted starch, acrylic acid grafted starch, polyacrylates, isobutylene-maleic anhydride co-polymers and combinations thereof; and (B) the hydrophilizing agent is a nonionic surfactant.

4. An absorbent composite according to claim 3 which has a dry density of from about 0.006 to 0.04 g/cm$^3$.

5. An absorbent composite according to claim 4 wherein the weight ratio of microfiber component to staple fiber component ranges from about 1:3 to 3:1.

6. An absorbent composite according to claim 5 which comprises
 (A) from about 20% to 65% by weight of the composite of the blown microfiber component; and
 (B) from about 10% to 60% by weight of the composite of the synthetic staple fiber component with substantially all of said staple fibers having a denier of from about 10 to 25.

7. An absorbent composite according to claim 6 wherein
 (A) the microfibers utilized are polypropylene microfibers;
 (B) the staple fibers utilized are polyethylene terephthalate staple fibers, substantially all of which have a fiber length between about 1.0 and 15 cm; and
 (C) the polymeric gelling agent utilized is selected from slightly cross-linked, partially neutralized polyacrylates and acrylic acid grafted starch, has an equilibrium gel volume of at least about 25 grams of artificial menses per gram of polymeric gelling agent and has an extractable polymer content in synthetic urine of no more than about 10% by weight.

8. An absorbent article of improved comfort, integrity and absorbency characteristics, said article comprising:
 (A) a liquid impervious backing sheet;
 (B) a liquid pervious hydrophobic topsheet; and
 (C) an absorbent structure according to claim 1 positioned between said backing sheet and said topsheet.

9. An absorbent article according to claim 8 wherein:
 (A) the microfibers utilized in the absorbent structure have an average diameter of from about 1 to 10 microns and comprise a polymeric material selected from polyolefins, polyesters, polyamides, polyacrylics and polystyrenes;
 (B) substantially all of the staple fibers utilized in the absorbent structure range in denier from about 10 to 25 and comprise a synthetic polymeric material selected from polyolefins, polyesters, polyacrylics, polyamides and polystyrenes;
 (C) the polymeric gelling agent in the absorbent structure has an equilibrium gel volume of at least about 25 grams of artificial menses per gram of polymeric gelling agent, a two minute gel volume which is at least 50% of the equilibrium gel volume, and an extractable polymer content in synthetic urine of no more than 10% by weight and comprises polymers selected from hydrolyzed acrylonitrile grafted starch, acrylic acid grafted starch, polyacrylates, isobutylene-maleic anhydride co-polymers and combinations thereof; and
 (D) the hydrophilizing agent used in the absorbent structure is a nonionic surfactant.

10. An absorbent article according to claim 9 wherein in the absorbent structure component:
 (A) the microfibers utilized are polypropylene microfibers;
 (B) the staple fibers utilized are polyethylene terephthalate staple fibers, substantially all of which have a fiber length between about 1.0 and 15 cm; and
 (C) the polymeric gelling agent utilized is selected from slightly cross-linked, partially neutralized polyacrylates and acrylic acid grafted starch, has an equilibrium gel volume of at least about 30 grams of artificial menses per gram of polymeric gelling agent and has an extractable polymer content in synthetic urine of no more than about 10% by weight.

11. A sanitary napkin of improved comfort, integrity and absorbency characteristics, said sanitary napkin comprising:
 (A) a liquid impervious backing sheet;
 (B) a liquid pervious hydrophobic topsheet; and
 (C) an absorbent core positioned between said backing sheet and said topsheet, said absorbent core comprising a composite web structure having longitudinal, transverse and thickness dimensions, said structure comprising
  (i) from about 30% to 50% by weight of the structure of blown microfibers which have an average diameter of from about 1 to 10 microns, said microfibers being formed from synthetic polymeric material selected from polyolefins, polyesters, polyamides, polyacrylics and polystyrenes;
  (ii) from about 25% to 55% by weight of the structure of substantially non-absorbent synthetic staple fibers, substantially all of which have a denier of from about 10 to 25, and a percent crimp of at least about 15%, said staple fibers being formed from synthetic polymeric material selected from polyolefins, polyesters, polyacrylics, polyamides and polystyrenes;
  (iii) from about 15% to 30% by weight of the structure of particles of a polymeric gelling agent having an equilibrium gel volume of at least about 20 grams of artificial menses per gram of gelling agent, a two-minute gel volume which is at least 40% of the equilibrium gel volume, and an extractable polymer content in synthetic urine of no more than about 17% by weight, with substantially all of said particles ranging in diameter from about 30 microns to 2 mm; and
  (iv) from about 0.01% to 10% by weight of the structure of a hydrophilizing agent which serves to hydrophilize the microfiber and staple fiber components; said hydrophilized microfibers, staple fibers and polymeric gelling agent particles being combined in a manner which forms a composite structure having a dry density of from about 0.006 to 0.03 g/cm$^3$ with said composite web structure further exhibiting both wet and dry resilience properties which enable such a composite web structure to recover to at least 50% of its original transverse dimension after compression to a transverse dimension which is 40% of its 60% of said original transverse dimension.

12. A sanitary napkin according to claim 11 wherein the absorbent core is wrapped in envelope tissue.

13. A sanitary napkin according to claim 12 wherein in the composite web structure of the absorbent core
 (A) the microfibers utilized ar polypropylene microfibers;

(B) the staple fibers utilized are polyethylene terephthalate staple fibers, substantially all of which have a fiber length between about 1.0 and 15 cm; and (C) the polymeric gelling agent utilized is selected from slightly cross-linked, partially neutralized polyacrylates and acrylic acid grafted starch, has an equilibrium gel volume of at least about 25 grams of artificial menses per gram of polymeric gelling agent and has an extractable polymer content in synthetic urine of no more than about 10% by weight.

14. A disposable diaper of improved comfort, integrity and absorbency characteristics, said diaper comprising (A) a liquid impervious backing sheet;
(B) a liquid pervious hydrophobic topsheet; and
(C) an absorbent core positioned between said backing sheet and said topsheet, said absorbent core comprising a composite web structure having longitudinal, transverse and thickness dimensions, said structure comprising (i) from about 30% to 70% by weight of the structure of blown microfibers which have an average diameter of from about 1 to 10 microns, said microfibers being formed from synthetic polymeric material selected from polyolefins, polyesters, polyamides, polyacrylics and polystyrenes;

(ii) from about 10% to 55% by weight of the structure of substantially non-absorbent synthetic staple fibers, substantially all of which have a denier of from about 10 to 25, and a percent crimp of at least about 15%, said staple fibers being formed from synthetic polymeric material selected from polyolefins, polyesters, polyacrylics, polyamides and polystyrenes;

(ii) from about 15% to 50% by weight of the structure of particles of a polymeric gelling agent having an equilibrium gel volume of at least about 30 grams of synthetic urine per gram of gelling agent, a two-minute gel volume which is at least 40% of the equilibrium gel volume, and an extractable polymer content in synthetic urine of no more than about 17% by weight, with substantially all of said particles ranging in diameter from about 30 microns to 2 mm; and (iv) from about 0.01% to 10% by weight of the structure of a hydrophilizing agent which serves to hydrophilize the microfiber and staple fiber components;

said hydrophilized microfibers, staple fibers and polymeric gelling agent particles being combined in a manner which forms a composite structure having a dry density of from about 0.01 to 0.04 g/cm$^3$; with said composite web structure further exhibiting both wet and dry resilience properties which enable such a composite web structure to recover to at least 50% of its original transverse dimension after compression to a transverse dimension which is 40% of its of said original transverse dimension.

15. A disposable diaper according to claim 14 wherein (A) said topsheet is co-extensive with one face of said core; and
(B) said backing sheet is co-extensive with the face of the core opposite the face covered by said topsheet and has a width greater than that of the core, to thereby provide side marginal portions of the backing sheet which extend beyond the core.

16. A disposable diaper according to claim 15 wherein the absorbent core is hourglass-shaped.

17. A disposable diaper according to claim 16 wherein in the composite web structure of the absorbent core (A) the microfibers utilized are polypropylene microfibers;
(B) the staple fibers utilized are polyethylene terephthalate staple fibers, substantially all of which have a fiber length between about 1.0 and 15 cm; and
(C) the polymeric gelling agent utilized is selected from slightly cross-linked, partially neutralized polyacrylates and acrylic acid grafted starch, has an equilibrium gel volume of at least about 30 grams of synthetic urine per gram of polymeric gelling agent and has an extractable polymer content in synthetic urine of no more than about 10% by weight.

18. Disposable training pants of improved comfort, integrity and absorbency, said training pants comprising (A) a non-woven, flexible substrate fashioned into a chassis in the form of briefs or shorts; and
(B) an absorbent core affixed in the crotch area of said chassis, said absorbent core comprising a composite web structure having longitudinal, transverse and thickness dimensions, said structure comprising (i) from about 30% to 70% by weight of the structure of blown microfibers which have an average diameter of from about 1 to 10 microns, said microfibers being formed from synthetic polymeric material selected from polyolefins, polyesters, polyamides, polyacrylics and polystyrenes;

(ii) from about 10% to 55% by weight of the structure of substantially non-absorbent synthetic staple fibers, substantially all of which have a denier of from about 10 to 25 and a percent crimp of at least about 15%, said staple fibers being formed from a synthetic polymeric material selected from polyolefins, polyesters, polyacrylics, polyamides and polystyrenes;

(iii) from about 15% to 50% by weight of the structure of particles of a polymeric gelling agent having an equilibrium librium gel volume of at least about 30 grams of synthetic urine per gram of gelling agent, a two-minute gel volume which is at least 40% of the equilibrium gel volume, and an extractable polymer content in synthetic urine of no more than about 17% by weight, with substantially all of said particles ranging in diameter from about 30 microns to 2 mm; and (iv) from about 0.01% to 10% by weight of the structure of a hydrophilizing agent which serves to hydrophilize the microfiber and staple fiber components;

said hydrophilized microfibers, staple fibers and polymeric gelling agent particles being combined in a manner which forms a composite structure having a dry density of from about 0.01 to 0.04 g/cm$^3$, with said composite web structure further exhibiting both wet and dry resilience properties which enable such a composite web structure to recover to at least 50% of its original transverse dimension after compression to a transverse dimension which is 40% of its original transverse dimension.

19. Disposable training pants according to claim 18 wherein the absorbent core is wrapped in envelope tissue.

20. Disposable training pants according to claim 19 wherein in the composite web structure of the absorbent core
(A) the microfibers utilized are polypropylene microfibers;
(B) the staple fibers utilized are polyethylene terephthalate staple fibers, substantially all of which have a fiber length between about 1.0 and 15 cm; and
(C) the polymeric gelling agent utilized is selected from slightly cross-linked, partially neutralized polyacrylates and acrylic acid grafted starch, has an equilibrium gel volume of at least about 30 grams of synthetic urine per gram of polymeric gelling agent and has an extractable polymer content in synthetic urine of no more than about 10% by weight.

* * * * *

UNITED STATES PATENT AND TRADEMARK OFFICE
CERTIFICATE OF CORRECTION

PATENT NO.   : 4,773,903
DATED        : September 27, 1988
INVENTOR(S)  : Paul T. Weisman, Thomas H. Daugherty, Thomas I. Insley, Jr.

It is certified that error appears in the above-identified patent and that said Letters Patent are hereby corrected as shown below:

Cover sheet, in the list of U.S. Patent Documents, delete "3,971,373 7/1976 Braun" and insert therefor --3,971,373  7/1976 Braun......... 128/146.2--.

Column 30, line 9, delete "table" and insert therefor --staple--.

Column 30, line 26, delete "an" and insert therefor --and--.

Column 30, line 54, delete "50%" and insert therefor --40%--.

Column 32, line 67, delete "ar" and insert therefor --are--.

Signed and Sealed this

Thirty-first Day of January, 1989

Attest:

DONALD J. QUIGG

*Attesting Officer*    *Commissioner of Patents and Trademarks*